US011135150B2

(12) United States Patent
Singer et al.

(10) Patent No.: US 11,135,150 B2
(45) Date of Patent: Oct. 5, 2021

(54) COMPOSITIONS AND METHODS FOR IMPROVING THE QUALITY OF CHEMICALLY TREATED HAIR

(71) Applicant: L'OREAL, Paris (FR)

(72) Inventors: Jim Singer, South Orange, NJ (US); Andrea Elsen, Linden, NJ (US)

(73) Assignee: L'OREAL, Paris (FR)

( * ) Notice: Subject to any disclaimer, the term of this patent is extended or adjusted under 35 U.S.C. 154(b) by 839 days.

(21) Appl. No.: 15/357,056

(22) Filed: Nov. 21, 2016

(65) Prior Publication Data
US 2018/0140531 A1    May 24, 2018

(51) Int. Cl.
*A61Q 5/08* (2006.01)
*A61K 8/81* (2006.01)
*A61K 8/365* (2006.01)
*A61Q 5/12* (2006.01)
*A61K 8/19* (2006.01)
*A61K 8/22* (2006.01)
*A61K 8/362* (2006.01)
*A61K 8/41* (2006.01)

(52) U.S. Cl.
CPC .............. *A61K 8/8164* (2013.01); *A61K 8/19* (2013.01); *A61K 8/22* (2013.01); *A61K 8/362* (2013.01); *A61K 8/365* (2013.01); *A61K 8/41* (2013.01); *A61Q 5/08* (2013.01); *A61Q 5/12* (2013.01); *A61K 2800/884* (2013.01)

(58) Field of Classification Search
None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,674,580 A | 4/1954 | Henkin |
| 2,850,351 A | 9/1958 | Moore et al. |
| 2,961,347 A | 11/1960 | Floyd |
| 3,142,623 A | 7/1964 | Zviak et al. |
| 3,193,464 A | 7/1965 | Edman et al. |
| 3,206,462 A | 9/1965 | McCarty |
| 3,227,615 A | 1/1966 | Korden |
| 3,288,770 A | 11/1966 | Butler |
| 3,412,019 A | 11/1968 | Hoover et al. |
| 3,472,243 A | 10/1969 | Wall et al. |
| 3,472,840 A | 10/1969 | Stone et al. |
| 3,589,978 A | 6/1971 | Kamal et al. |
| 3,632,559 A | 1/1972 | Matter et al. |
| 3,766,267 A | 10/1973 | Zak et al. |
| 3,840,656 A | 10/1974 | Kalopissis et al. |
| 3,874,870 A | 4/1975 | Green et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,003,699 A | 1/1977 | Rose et al. |
| 4,005,193 A | 1/1977 | Green et al. |
| 4,012,398 A | 3/1977 | Conner et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,166,894 A | 9/1979 | Schaper |
| 4,172,887 A | 10/1979 | Vanlerberghe et al. |
| RE30,199 E | 1/1980 | Rose et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |

(Continued)

FOREIGN PATENT DOCUMENTS

| | | |
|---|---|---|
| CN | 1383377 A | 12/2002 |
| CN | 1423548 A | 6/2003 |

(Continued)

OTHER PUBLICATIONS

Non-Final Office Action for copending U.S. Appl. No. 15/604,189, dated Apr. 8, 2019.
International Search Report and Written Opinion for counterpart Application No. PCT/US2018/034371, dated Nov. 16, 2018.
Mintel: "Hydrating Hair Colour," Garnier, Jan. 2017, pp. 1-6.
Final Office Action for copending U.S. Appl. No. 15/603,889, dated Jul. 12, 2019.
Non-Final Office Action for copending U.S. Appl. No. 15/603,889, dated Jan. 2, 2019.
International Search Report and Written Opinion for counterpart Application No. PCT/US2018/034378, dated Jul. 24, 2018.
Final Office Action for copending U.S. Appl. No. 16/234,883, dated Mar. 11, 2020.
Final Office Action for copending U.S. Appl. No. 16/176,350, dated Apr. 8, 2020.

(Continued)

*Primary Examiner* — Jyothsna A Venkat
(74) *Attorney, Agent, or Firm* — The Marbury Law Group, PLLC

(57) ABSTRACT

The present disclosure relates to hair care compositions for chemically treating hair, to kits comprising the compositions, and to methods for treating hair with the compositions. The compositions include one or more polymeric acid compounds and/or polymeric acid anhydride compounds in addition to one or more active agents for chemically treating the hair. Additionally, the compositions can optionally include one or more non-polymeric, mono-, di-, and/or tri-carboxylic acids and/or one or more mono- and/or di-amines and/or polyamines. Hair treated with the compositions exhibits improved softness, smoothness, and discipline.

14 Claims, No Drawings

(56) References Cited

U.S. PATENT DOCUMENTS

| | | |
|---|---|---|
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,412,943 A | 11/1983 | Hirota et al. |
| 4,422,853 A | 12/1983 | Jacquet et al. |
| 4,425,132 A | 1/1984 | Grollier et al. |
| 4,532,950 A | 8/1985 | Lang et al. |
| 4,579,732 A | 4/1986 | Grollier et al. |
| 4,591,610 A | 5/1986 | Grollier |
| 4,608,250 A | 8/1986 | Jacquet et al. |
| 4,734,277 A | 3/1988 | Login |
| 4,761,273 A | 8/1988 | Grollier et al. |
| 4,770,873 A | 9/1988 | Wolfram et al. |
| 4,772,462 A | 9/1988 | Boothe et al. |
| 4,777,040 A | 10/1988 | Grollier et al. |
| 4,793,992 A | 12/1988 | Mathews et al. |
| 4,793,993 A | 12/1988 | Siuta-Mangano et al. |
| 4,812,307 A | 3/1989 | Siuta-Mangano |
| 4,834,971 A | 5/1989 | Klenk et al. |
| 4,906,460 A | 3/1990 | Kim et al. |
| 4,948,579 A | 8/1990 | Jacquet et al. |
| 4,970,066 A | 11/1990 | Grollier et al. |
| 5,061,289 A | 10/1991 | Clausen et al. |
| 5,085,860 A | 2/1992 | Junino et al. |
| 5,143,518 A | 9/1992 | Madrange et al. |
| 5,196,189 A | 3/1993 | Jacquet et al. |
| 5,221,286 A | 6/1993 | Singleton et al. |
| 5,293,885 A | 3/1994 | Darkwa et al. |
| 5,350,572 A | 9/1994 | Savaides et al. |
| 5,356,438 A | 10/1994 | Kim et al. |
| 5,380,340 A | 1/1995 | Neunhoeffer et al. |
| 5,534,267 A | 7/1996 | Neunhoeffer et al. |
| 5,565,216 A | 10/1996 | Cowsar et al. |
| 5,593,662 A | 1/1997 | Deckner et al. |
| 5,616,150 A | 4/1997 | Moeller et al. |
| 5,628,991 A | 5/1997 | Samain et al. |
| 5,635,168 A | 6/1997 | Burns et al. |
| 5,651,960 A | 7/1997 | Chan et al. |
| 5,656,265 A | 8/1997 | Bailey et al. |
| 5,663,366 A | 9/1997 | Neunhoeffer et al. |
| 5,688,291 A | 11/1997 | Said et al. |
| 5,708,151 A | 1/1998 | Möckli |
| 5,766,576 A | 6/1998 | Löwe et al. |
| 5,811,085 A | 9/1998 | Halloran |
| 5,833,966 A | 11/1998 | Samain |
| 5,869,068 A | 2/1999 | De Lacharriere et al. |
| 5,951,969 A | 9/1999 | Golinski et al. |
| 5,972,322 A | 10/1999 | Rath et al. |
| 5,985,803 A | 11/1999 | Rizvi et al. |
| 6,013,250 A | 1/2000 | Cannell et al. |
| 6,015,574 A | 1/2000 | Cannell et al. |
| 6,036,966 A | 3/2000 | Youssefyeh |
| 6,090,762 A | 7/2000 | Clapperton et al. |
| 6,099,592 A | 8/2000 | Vidal et al. |
| 6,173,717 B1 | 1/2001 | Schonert et al. |
| 6,241,971 B1 | 6/2001 | Fox et al. |
| 6,284,003 B1 | 9/2001 | Rose et al. |
| 6,309,426 B1 | 10/2001 | Dias et al. |
| 6,338,741 B1 | 1/2002 | Vidal et al. |
| 6,348,189 B1 | 2/2002 | Tanabe et al. |
| 6,348,200 B1 | 2/2002 | Nakajima et al. |
| 6,398,821 B1 | 6/2002 | Dias et al. |
| 6,458,906 B1 | 10/2002 | Torgerson et al. |
| 6,488,945 B2 | 12/2002 | Sato |
| 6,515,050 B1 | 2/2003 | Mitsuzuka et al. |
| 6,537,532 B1 | 3/2003 | Torgerson et al. |
| 6,569,412 B2 | 5/2003 | Yamaguchi et al. |
| 6,645,258 B2 | 11/2003 | Vidal et al. |
| 6,645,478 B2 | 11/2003 | Rollat et al. |
| 6,669,933 B2 | 12/2003 | Duffer et al. |
| 6,706,258 B1 | 3/2004 | Gallagher et al. |
| 6,730,789 B1 | 5/2004 | Birault et al. |
| 6,767,875 B1 | 7/2004 | Snyder et al. |
| 6,979,439 B1 | 12/2005 | Sakai et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,135,167 B2 | 11/2006 | Legrand et al. |
| 7,147,843 B2 | 12/2006 | Yoshida et al. |
| 7,151,079 B2 | 12/2006 | Fack et al. |
| 7,204,861 B2 | 4/2007 | Marsh et al. |
| 7,390,479 B2 | 6/2008 | Sockel et al. |
| 7,427,656 B2 | 9/2008 | Decarolis et al. |
| 7,495,037 B2 | 2/2009 | Moszner et al. |
| 7,598,213 B2 | 10/2009 | Geary et al. |
| 7,612,141 B2 | 11/2009 | Sakai et al. |
| 7,815,901 B2 | 10/2010 | Mathonneau et al. |
| 7,905,926 B2 | 3/2011 | DeGeorge et al. |
| 7,915,208 B2 | 3/2011 | Roso et al. |
| 7,931,698 B2 | 4/2011 | Simonet et al. |
| 7,972,388 B2 | 7/2011 | Hamilton et al. |
| 7,981,405 B2 | 7/2011 | Ueyama et al. |
| 8,163,861 B2 | 4/2012 | Puerta et al. |
| 8,288,329 B2 | 10/2012 | Hata et al. |
| 8,298,519 B2 | 10/2012 | Adams et al. |
| 8,357,356 B2 | 1/2013 | Zaeska et al. |
| 8,388,701 B2 | 3/2013 | Uellner et al. |
| 8,513,200 B2 | 8/2013 | Dixon et al. |
| 8,613,913 B2 | 12/2013 | Chang et al. |
| 8,632,758 B2 | 1/2014 | Terada |
| 8,642,021 B2 | 2/2014 | Brautigam et al. |
| 8,642,659 B2 | 2/2014 | Springer et al. |
| 8,921,292 B2 | 12/2014 | Fujita et al. |
| 9,095,518 B2 | 8/2015 | Pressly et al. |
| 9,144,537 B1 | 9/2015 | Pressly et al. |
| 9,175,114 B2 | 11/2015 | Puerta et al. |
| 9,180,086 B2 | 11/2015 | Cabourg et al. |
| 9,283,156 B2 | 3/2016 | Savaides et al. |
| 9,326,926 B2 | 5/2016 | Pressly et al. |
| 9,402,796 B2 | 8/2016 | Briggs et al. |
| 9,498,419 B2 | 11/2016 | Pressly et al. |
| 9,597,273 B2 | 3/2017 | Pressly et al. |
| 9,610,241 B2 | 4/2017 | Cabourg et al. |
| 9,849,071 B2 | 12/2017 | Fack et al. |
| 9,918,923 B1 | 3/2018 | Naiberk et al. |
| 9,993,406 B2 | 6/2018 | Manneck et al. |
| 10,004,673 B1 | 6/2018 | Elsen-Wahrer et al. |
| 10,085,931 B2 | 10/2018 | Baghdadli et al. |
| 10,231,915 B2 | 3/2019 | Dreher et al. |
| 10,561,599 B2 | 2/2020 | Patterson et al. |
| 10,576,307 B2 | 3/2020 | Patterson et al. |
| 2001/0029637 A1 | 10/2001 | Nakashimada et al. |
| 2001/0042276 A1 | 11/2001 | Kawasoe et al. |
| 2001/0052354 A1 | 12/2001 | Nishibe et al. |
| 2002/0029429 A1 | 3/2002 | Dias et al. |
| 2002/0032933 A1 | 3/2002 | Dias et al. |
| 2002/0050013 A1 | 5/2002 | Vidal et al. |
| 2002/0053110 A1 | 5/2002 | Dias et al. |
| 2002/0155081 A1 | 10/2002 | Coope |
| 2002/0189034 A1 | 12/2002 | Kitabata et al. |
| 2003/0012761 A1 | 1/2003 | Yoshida et al. |
| 2003/0019051 A9 | 1/2003 | Vidal et al. |
| 2003/0049222 A1 | 3/2003 | Akhter et al. |
| 2003/0072962 A1 | 4/2003 | Matsuzaki et al. |
| 2003/0083380 A1 | 5/2003 | Yu et al. |
| 2003/0152543 A1 | 8/2003 | Legrand et al. |
| 2003/0215415 A1 | 11/2003 | Mitsumatsu et al. |
| 2004/0034944 A1 | 2/2004 | Legrand et al. |
| 2004/0034946 A1 | 2/2004 | Legrand et al. |
| 2004/0067212 A1 | 4/2004 | Tokuyama et al. |
| 2004/0086475 A1 | 5/2004 | Boswell et al. |
| 2004/0088800 A1 | 5/2004 | Cotteret |
| 2004/0156877 A1 | 8/2004 | Tokuyama et al. |
| 2004/0181883 A1 | 9/2004 | Legrand et al. |
| 2004/0202689 A1 | 10/2004 | Subramanyan et al. |
| 2004/0216244 A1 | 11/2004 | Cotteret et al. |
| 2004/0228580 A1 | 11/2004 | Lee et al. |
| 2004/0241114 A1 | 12/2004 | Gupta |
| 2004/0256598 A1 | 12/2004 | Plos et al. |
| 2004/0258652 A1 | 12/2004 | Pascaly et al. |
| 2005/0036970 A1 | 2/2005 | Sabbagh et al. |
| 2005/0087718 A1 | 4/2005 | Okada |
| 2005/0095215 A1 | 5/2005 | Popp |

(56) References Cited

U.S. PATENT DOCUMENTS

| | | |
|---|---|---|
| 2005/0176615 A1 | 8/2005 | Kinoshita et al. |
| 2005/0186164 A1 | 8/2005 | Akyuz |
| 2005/0191263 A1 | 9/2005 | Ueyama et al. |
| 2005/0193501 A1 | 9/2005 | Chan et al. |
| 2005/0201966 A1 | 9/2005 | Ueyama et al. |
| 2006/0024257 A1 | 2/2006 | Chang et al. |
| 2006/0075580 A1 | 4/2006 | Chan et al. |
| 2006/0093571 A1 | 5/2006 | Glinski |
| 2006/0135397 A1 | 6/2006 | Bissey-Beugras et al. |
| 2006/0166845 A1 | 7/2006 | Terada |
| 2006/0182702 A1 | 8/2006 | Lazzeri et al. |
| 2006/0198807 A1 | 9/2006 | Morioka |
| 2006/0228316 A1 | 10/2006 | Cannell et al. |
| 2006/0251673 A1 | 11/2006 | Hwang et al. |
| 2007/0041921 A1 | 2/2007 | Neill et al. |
| 2007/0067924 A1 | 3/2007 | Beck et al. |
| 2007/0107142 A1 | 5/2007 | Nguyen et al. |
| 2007/0116661 A1 | 5/2007 | Mata |
| 2007/0160560 A1 | 7/2007 | Laurent et al. |
| 2007/0161543 A1 | 7/2007 | Yu et al. |
| 2007/0190008 A1 | 8/2007 | Campain et al. |
| 2007/0261594 A1 | 11/2007 | Vaskelis et al. |
| 2007/0264208 A1 | 11/2007 | Mougin et al. |
| 2008/0025937 A1 | 1/2008 | Cassier |
| 2008/0025939 A1 | 1/2008 | Cassier et al. |
| 2008/0066773 A1 | 3/2008 | Anderson et al. |
| 2008/0118458 A1 | 5/2008 | Giesen et al. |
| 2008/0124295 A1 | 5/2008 | Duranton et al. |
| 2008/0138309 A1 | 6/2008 | Malle et al. |
| 2008/0141468 A1 | 6/2008 | Cotteret |
| 2008/0187506 A1 | 8/2008 | Carballada et al. |
| 2008/0226576 A1 | 9/2008 | Benabdillah et al. |
| 2008/0233072 A1 | 9/2008 | Bureiko et al. |
| 2008/0306025 A1 | 12/2008 | Yu et al. |
| 2009/0022681 A1 | 1/2009 | Carballada et al. |
| 2009/0041699 A1 | 2/2009 | Molenda et al. |
| 2009/0041701 A1 | 2/2009 | Taylor |
| 2009/0041713 A1 | 2/2009 | Taylor |
| 2009/0053165 A1* | 2/2009 | Brown ............... A61K 8/0295 424/78.08 |
| 2009/0071493 A1 | 3/2009 | Nguyen et al. |
| 2009/0126756 A1 | 5/2009 | Syed et al. |
| 2009/0208499 A1 | 8/2009 | Yu et al. |
| 2009/0214628 A1 | 8/2009 | de Rijk |
| 2009/0252697 A1 | 10/2009 | Barbarat et al. |
| 2009/0274677 A1 | 11/2009 | Isaacs et al. |
| 2010/0004391 A1 | 1/2010 | Haddleton et al. |
| 2010/0015079 A1 | 1/2010 | Schrader |
| 2010/0081716 A1 | 4/2010 | Matsunaga et al. |
| 2010/0119468 A1 | 5/2010 | Garcia Castro et al. |
| 2010/0154140 A1 | 6/2010 | Simonet et al. |
| 2010/0158845 A1 | 6/2010 | Ellington et al. |
| 2010/0158964 A1 | 6/2010 | Cunningham et al. |
| 2010/0178267 A1 | 7/2010 | Puerta et al. |
| 2010/0189795 A1 | 7/2010 | Dreher |
| 2010/0202998 A1 | 8/2010 | Ramos-Stanbury et al. |
| 2010/0247463 A1 | 9/2010 | Yu et al. |
| 2010/0303748 A1 | 12/2010 | Hercouet |
| 2011/0056508 A1 | 3/2011 | Gross et al. |
| 2011/0061671 A1 | 3/2011 | Neplaz et al. |
| 2011/0150804 A1 | 6/2011 | Nojiri et al. |
| 2011/0213033 A1 | 9/2011 | Tokuyama et al. |
| 2011/0256084 A1 | 10/2011 | Dixon et al. |
| 2011/0311463 A1 | 12/2011 | Diamond et al. |
| 2012/0015894 A1 | 1/2012 | Terada |
| 2012/0022037 A1 | 1/2012 | Terada |
| 2012/0064137 A1 | 3/2012 | Kawai |
| 2012/0114583 A1 | 5/2012 | Giesen et al. |
| 2012/0118316 A1 | 5/2012 | Uellner et al. |
| 2012/0121705 A1 | 5/2012 | Paus et al. |
| 2012/0180807 A1 | 7/2012 | Flohr |
| 2012/0244082 A1 | 9/2012 | Sulzbach et al. |
| 2012/0288459 A1 | 11/2012 | Burg et al. |
| 2012/0329650 A1 | 12/2012 | Lopez-Cervantes |
| 2013/0016246 A1 | 1/2013 | Hatanaka et al. |
| 2013/0034515 A1 | 2/2013 | Stone et al. |
| 2013/0102513 A1 | 4/2013 | Terada |
| 2013/0118996 A1 | 5/2013 | Kaplan |
| 2013/0149274 A1 | 6/2013 | Nguyen et al. |
| 2013/0152959 A1 | 6/2013 | Genain et al. |
| 2013/0156716 A1 | 6/2013 | Yontz |
| 2013/0164240 A1 | 6/2013 | Schrott |
| 2013/0172518 A1 | 7/2013 | Huang et al. |
| 2013/0216491 A1 | 8/2013 | Ogihara et al. |
| 2013/0233331 A1 | 9/2013 | Khenniche et al. |
| 2013/0233332 A1 | 9/2013 | Khenniche et al. |
| 2013/0251656 A1 | 9/2013 | Khenniche et al. |
| 2013/0266529 A1 | 10/2013 | Deconinck et al. |
| 2013/0280199 A1 | 10/2013 | Albert et al. |
| 2013/0309190 A1* | 11/2013 | Dimotakis ............... A61Q 5/06 424/70.17 |
| 2013/0315852 A1 | 11/2013 | Streuli |
| 2014/0120047 A1 | 5/2014 | Krueger |
| 2014/0158150 A1 | 6/2014 | Schoepgens et al. |
| 2014/0170105 A1 | 6/2014 | Chen et al. |
| 2014/0171354 A1 | 6/2014 | Miralles et al. |
| 2014/0186283 A1 | 7/2014 | Cabourg et al. |
| 2014/0196741 A1 | 7/2014 | Cabourg et al. |
| 2014/0246041 A1 | 9/2014 | Krueger |
| 2015/0004117 A1 | 1/2015 | Tan et al. |
| 2015/0004119 A1 | 1/2015 | Tan et al. |
| 2015/0034117 A1 | 2/2015 | Pressly et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0053228 A1 | 2/2015 | Bonauer et al. |
| 2015/0053230 A1 | 2/2015 | Myatt |
| 2015/0090285 A1 | 4/2015 | Worner et al. |
| 2015/0157544 A1 | 6/2015 | Briggs et al. |
| 2015/0252302 A1 | 9/2015 | Rieth et al. |
| 2015/0283041 A1 | 10/2015 | Benn et al. |
| 2015/0290101 A1 | 10/2015 | Pressly et al. |
| 2015/0297496 A1 | 10/2015 | Kroon et al. |
| 2015/0313816 A1 | 11/2015 | Daubresse |
| 2015/0328102 A1 | 11/2015 | Pressly et al. |
| 2016/0058688 A1 | 3/2016 | Anderheggen et al. |
| 2016/0081899 A1 | 3/2016 | Pressly et al. |
| 2016/0166479 A1 | 6/2016 | Chiou et al. |
| 2016/0175238 A1 | 6/2016 | Shin et al. |
| 2016/0193129 A1 | 7/2016 | Pressly et al. |
| 2016/0235649 A1 | 8/2016 | Streuli |
| 2016/0263003 A1 | 9/2016 | Pressly et al. |
| 2016/0310394 A1 | 10/2016 | Pressly et al. |
| 2016/0331664 A1* | 11/2016 | Anderheggen ........... A61K 8/22 |
| 2016/0348037 A1 | 12/2016 | Findlay et al. |
| 2017/0007518 A1 | 1/2017 | Everaert et al. |
| 2017/0112740 A1 | 4/2017 | Schoepgens et al. |
| 2017/0112743 A1 | 4/2017 | Schoepgens et al. |
| 2017/0113071 A1 | 4/2017 | Schoepgens et al. |
| 2017/0119122 A1 | 5/2017 | Rautenberg-Groth et al. |
| 2017/0128334 A1 | 5/2017 | Schoepgens et al. |
| 2017/0128342 A1 | 5/2017 | Schoepgens et al. |
| 2017/0143611 A1 | 5/2017 | Hippe et al. |
| 2017/0151143 A1 | 6/2017 | Scheunemann et al. |
| 2017/0151144 A1 | 6/2017 | Scheunemann et al. |
| 2017/0151146 A1 | 6/2017 | Scheunemann et al. |
| 2017/0151147 A1 | 6/2017 | Scheunemann et al. |
| 2017/0151156 A1 | 6/2017 | Scheunemann et al. |
| 2017/0157011 A1 | 6/2017 | Punyani et al. |
| 2017/0165161 A1 | 6/2017 | Manneck et al. |
| 2017/0202763 A1 | 7/2017 | Manneck et al. |
| 2017/0246094 A1 | 8/2017 | Dreher et al. |
| 2017/0360658 A1 | 12/2017 | Ferrari et al. |
| 2018/0055751 A1 | 3/2018 | Gevgilili et al. |
| 2018/0116942 A1 | 5/2018 | Mahadeshwar et al. |
| 2018/0140532 A1 | 5/2018 | Singer et al. |
| 2018/0280267 A1 | 10/2018 | Rughani et al. |
| 2018/0280269 A1 | 10/2018 | Rughani et al. |
| 2018/0280270 A1 | 10/2018 | Rughani et al. |
| 2018/0280271 A1 | 10/2018 | Fack et al. |
| 2018/0338895 A1 | 11/2018 | Patterson et al. |
| 2018/0338901 A1 | 11/2018 | Patterson et al. |
| 2018/0339175 A1 | 11/2018 | Patterson et al. |
| 2019/0160000 A1 | 5/2019 | Herrlein et al. |

(56) References Cited

U.S. PATENT DOCUMENTS

| | | | |
|---|---|---|---|
| 2019/0201309 A1 | 7/2019 | Machover et al. | |
| 2019/0254954 A1 | 8/2019 | Jegou et al. | |
| 2020/0129405 A1 | 4/2020 | Mitchell et al. | |

FOREIGN PATENT DOCUMENTS

| | | | |
|---|---|---|---|
| CN | 1424016 A | 6/2003 | |
| CN | 1454074 A | 11/2003 | |
| CN | 1678281 A | 10/2005 | |
| CN | 1717215 A | 1/2006 | |
| CN | 1778289 A | 5/2006 | |
| CN | 1798539 A | 7/2006 | |
| CN | 101282705 A | 10/2008 | |
| CN | 101495087 A | 7/2009 | |
| CN | 101686920 A | 3/2010 | |
| CN | 101843561 A | 9/2010 | |
| CN | 101966136 A | 2/2011 | |
| CN | 102056896 A | 5/2011 | |
| CN | 102166163 A | 8/2011 | |
| CN | 102231974 A | 11/2011 | |
| CN | 102281864 A | 12/2011 | |
| CN | 102361627 A | 2/2012 | |
| CN | 102397232 A | 4/2012 | |
| CN | 102451117 A | 5/2012 | |
| CN | 103356395 A | 10/2013 | |
| CN | 103998099 A | 8/2014 | |
| CN | 104066419 A | 9/2014 | |
| CN | 104159567 A | 11/2014 | |
| CN | 104519962 A | 4/2015 | |
| CN | 105267066 A | 1/2016 | |
| CN | 105902403 A | 8/2016 | |
| CN | 105902404 A | 8/2016 | |
| CN | 106265109 A | 1/2017 | |
| DE | 1220969 B | 7/1966 | |
| DE | 2225541 A1 | 12/1973 | |
| DE | 2359399 A1 | 6/1975 | |
| DE | 3843892 A1 | 6/1990 | |
| DE | 4133957 A1 | 4/1993 | |
| DE | 4300320 A1 | 7/1994 | |
| DE | 19543988 A1 | 5/1997 | |
| DE | 10051773 A1 | 4/2002 | |
| DE | 10051774 A1 | 4/2002 | |
| DE | 102004052480 A1 | 5/2006 | |
| DE | 10 2007 039745 A1 | 2/2009 | |
| DE | 202015104742 U1 | 10/2015 | |
| DE | 102014213317 A1 | 1/2016 | |
| DE | 102015223828 A1 | 9/2016 | |
| DE | 102015221460 A1 | 5/2017 | |
| DE | 102016200688 A1 | 7/2017 | |
| DE | 202017001430 | 7/2017 | |
| EP | 0122324 A1 | 10/1984 | |
| EP | 0159628 A2 | 10/1985 | |
| EP | 0286261 A2 | 10/1988 | |
| EP | 0299764 A2 | 1/1989 | |
| EP | 02898684 A2 | 1/1989 | |
| EP | 0512879 A2 | 11/1992 | |
| EP | 0636358 A1 | 2/1995 | |
| EP | 0714954 A2 | 6/1996 | |
| EP | 0770375 A1 | 5/1997 | |
| EP | 0855178 A2 | 7/1998 | |
| EP | 0978272 A1 | 2/2000 | |
| EP | 1118319 A1 | 7/2001 | |
| EP | 1174112 A2 | 1/2002 | |
| EP | 1541117 A1 | 6/2005 | |
| EP | 1570832 A1 | 9/2005 | |
| EP | 1779896 A2 | 5/2007 | |
| EP | 1810657 A1 | 7/2007 | |
| EP | 2123250 A1 | 11/2009 | |
| EP | 2165697 A1 | 3/2010 | |
| EP | 2229933 A1 | 9/2010 | |
| EP | 2295029 A1 | 3/2011 | |
| EP | 2460511 A1 | 6/2012 | |
| EP | 2471504 A1 | 7/2012 | |
| EP | 2478892 A1 | 7/2012 | |
| EP | 1510197 B1 | 3/2016 | |
| FR | 1492597 A | 8/1967 | |
| FR | 1583363 A | 10/1969 | |
| FR | 2162025 A | 7/1973 | |
| FR | 2252840 A1 | 6/1975 | |
| FR | 2270846 A1 | 12/1975 | |
| FR | 2280361 A2 | 2/1976 | |
| FR | 2316271 A1 | 1/1977 | |
| FR | 2320330 A1 | 3/1977 | |
| FR | 2336434 A1 | 7/1977 | |
| FR | 2368508 A2 | 5/1978 | |
| FR | 2413907 A1 | 8/1979 | |
| FR | 2505348 A1 | 11/1982 | |
| FR | 2542997 A1 | 9/1984 | |
| FR | 2733749 A1 | 11/1996 | |
| FR | 2789895 A1 | 8/2000 | |
| FR | 2789896 A1 | 8/2000 | |
| FR | 2801308 A1 | 5/2001 | |
| FR | 2841129 A1 | 12/2003 | |
| FR | 2886136 A1 | 12/2006 | |
| FR | 2939030 A1 | 6/2010 | |
| FR | 2944441 A1 | 10/2010 | |
| FR | 2966352 A1 | 4/2012 | |
| FR | 2975899 A1 | 12/2012 | |
| FR | 2975900 A1 | 12/2012 | |
| GB | 713675 A | 8/1954 | |
| GB | 741307 A | 11/1955 | |
| GB | 773559 A | 4/1957 | |
| GB | 1026978 A | 4/1966 | |
| GB | 1125794 A | 8/1968 | |
| GB | 1153196 A | 5/1969 | |
| GB | 1260451 A | 1/1972 | |
| GB | 1546809 A | 5/1979 | |
| GB | 1584364 A | 2/1981 | |
| JP | 63154611 A | 6/1988 | |
| JP | S63-255214 A | 10/1988 | |
| JP | 02-019576 A | 1/1990 | |
| JP | H02-138110 A | 5/1990 | |
| JP | 05/163124 A | 6/1993 | |
| JP | H07-069847 A | 3/1995 | |
| JP | 08-198732 A | 8/1996 | |
| JP | H08-509478 A | 10/1996 | |
| JP | 2000-229821 A | 8/2000 | |
| JP | 2001-081013 A | 3/2001 | |
| JP | 2002-097115 A | 4/2002 | |
| JP | 2002-105493 A | 4/2002 | |
| JP | 2002-121121 A | 4/2002 | |
| JP | 2002-356408 A | 12/2002 | |
| JP | 2002-363048 A | 12/2002 | |
| JP | 2003-095876 A | 4/2003 | |
| JP | 2003-516335 A | 5/2003 | |
| JP | 2004-026976 A | 1/2004 | |
| JP | 2005-060398 A | 3/2005 | |
| JP | 2005-154348 A | 6/2005 | |
| JP | 2006-219493 A | 8/2006 | |
| JP | 2006-327994 A | 12/2006 | |
| JP | 2008-189686 A | 8/2008 | |
| JP | 2009-007283 A | 1/2009 | |
| JP | 2009-536619 A | 10/2009 | |
| JP | 2010-155823 A | 7/2010 | |
| JP | 2012-515218 A | 7/2012 | |
| JP | 2013-500328 A | 1/2013 | |
| JP | 2016-003185 A | 1/2016 | |
| JP | 2017-095451 A | 6/2017 | |
| JP | 2018-514570 A | 6/2018 | |
| KR | 10-2001-0039848 A | 7/2001 | |
| KR | 2003-0003970 A | 1/2003 | |
| KR | 10-2004-0098688 A | 11/2004 | |
| KR | 10-2006-0059564 A | 6/2006 | |
| KR | 10-2012-0062511 A | 6/2012 | |
| KR | 10-2016-0064420 A | 6/2016 | |
| RU | 2144945 C1 | 1/2000 | |
| RU | 2229281 C1 | 5/2004 | |
| WO | 93/00882 A1 | 1/1993 | |
| WO | 93/08787 A2 | 5/1993 | |
| WO | 94/08969 A1 | 4/1994 | |
| WO | 94/08970 A1 | 4/1994 | |
| WO | 95/01152 A1 | 1/1995 | |
| WO | 95/01772 A1 | 1/1995 | |
| WO | 95/15144 A1 | 6/1995 | |

(56) References Cited

FOREIGN PATENT DOCUMENTS

| | | |
|---|---|---|
| WO | 96/15765 A1 | 5/1996 |
| WO | 97/24106 A1 | 7/1997 |
| WO | 98/56333 A1 | 12/1998 |
| WO | 99/11226 A1 | 3/1999 |
| WO | 99/66793 A1 | 12/1999 |
| WO | 01/35912 A1 | 5/2001 |
| WO | 01/47486 A1 | 7/2001 |
| WO | 02/19976 A1 | 3/2002 |
| WO | 02/32383 A2 | 4/2002 |
| WO | 02/32386 A2 | 4/2002 |
| WO | 02/055034 A2 | 7/2002 |
| WO | 2004/019858 A2 | 3/2004 |
| WO | 2005/058258 A1 | 6/2005 |
| WO | 2006/011771 A1 | 2/2006 |
| WO | 2006/134051 A1 | 12/2006 |
| WO | 2007/003307 A1 | 1/2007 |
| WO | 2007/038733 A1 | 4/2007 |
| WO | 2009/024936 A2 | 2/2009 |
| WO | 2010/015517 A2 | 2/2010 |
| WO | 2010/049434 A2 | 5/2010 |
| WO | 2011/134785 A2 | 11/2011 |
| WO | 2012/033813 A2 | 3/2012 |
| WO | 2012/080321 A2 | 6/2012 |
| WO | 2012/084532 A2 | 6/2012 |
| WO | 2012/084876 A2 | 6/2012 |
| WO | 2012/164064 A1 | 12/2012 |
| WO | 2013/092080 A1 | 6/2013 |
| WO | 2013/136480 A1 | 9/2013 |
| WO | 2014/016407 A1 | 1/2014 |
| WO | 2014/072490 A1 | 5/2014 |
| WO | 2014/118212 A1 | 8/2014 |
| WO | 2014/125452 A1 | 8/2014 |
| WO | 2014/144076 A1 | 9/2014 |
| WO | 2014/167508 A1 | 10/2014 |
| WO | 2014/207097 A1 | 12/2014 |
| WO | 2015/017768 A1 | 2/2015 |
| WO | 2015/026994 A1 | 2/2015 |
| WO | 2015/033351 A1 | 3/2015 |
| WO | 2015/058942 A1 | 4/2015 |
| WO | 2015/069823 al | 5/2015 |
| WO | 2015/075064 A2 | 5/2015 |
| WO | 2015/118357 A1 | 8/2015 |
| WO | 2015/175986 A2 | 11/2015 |
| WO | 2016/005114 A1 | 1/2016 |
| WO | 2016/005144 A1 | 1/2016 |
| WO | 2016/069877 A1 | 5/2016 |
| WO | 2016/091492 A1 | 6/2016 |
| WO | 2016/098870 A1 | 6/2016 |
| WO | 2016/100885 A1 | 6/2016 |
| WO | 2016/102543 A1 | 6/2016 |
| WO | 2016/120642 A1 | 8/2016 |
| WO | 2016/161360 A1 | 10/2016 |
| WO | 2016/179017 A1 | 11/2016 |
| WO | 2016/198203 A1 | 12/2016 |
| WO | 2016/207840 A1 | 12/2016 |
| WO | 2017/041903 A1 | 3/2017 |
| WO | 2017/041905 A1 | 3/2017 |
| WO | 2017/041906 A1 | 3/2017 |
| WO | 2017/041907 A1 | 3/2017 |
| WO | 2017/041908 A1 | 3/2017 |
| WO | 2017/041909 A1 | 3/2017 |
| WO | 2017/041910 A1 | 3/2017 |
| WO | 2017/059646 A1 | 4/2017 |
| WO | 2017/085117 A1 | 5/2017 |
| WO | 2017/091794 A1 | 6/2017 |
| WO | 2017/091796 A1 | 6/2017 |
| WO | 2017/091797 A1 | 6/2017 |
| WO | 2017/091800 A1 | 6/2017 |
| WO | 2017/102855 A1 | 6/2017 |
| WO | 2017/102936 A1 | 6/2017 |
| WO | 2017/207198 A1 | 12/2017 |
| WO | 2018/081399 A1 | 5/2018 |
| WO | 2018/085478 A1 | 5/2018 |

OTHER PUBLICATIONS

Non-Final Office Action for copending U.S. Appl. No. 16/176,350, dated Nov. 14, 2019.
International Search Report and Written Opinion for counterpart Application No. PCT/US2019/059002, dated Feb. 4, 2020.
Korean Notification of Reasons for Refusal of counterpart Application No. KR10-2017-7034789, dated May 19, 2020.
Non-Final Office Action for copending U.S. Appl. No. 16/234,883, dated Sep. 16, 2019.
International Search Report and Written Opinion for counterpart Application No. PCT/US2018/067814, dated Feb. 25, 2019.
Final Office Action for copending U.S. Appl. No. 15/942,042, dated Jun. 1, 2020.
Japanese Notice of Reasons for Refusal for Application No. 2017-557074, dated Jun. 1, 2020.
Non-Final Office Action for copending U.S. Appl. No. 15/942,085, dated Jun. 19, 2020.
Mintel, "Masque Force Architecte Reconstructing Masque," L'Oreal, Feb. 2012, pp. 1-6.
Shiseido Super Mild Hair Care—Shampoo and Conditioner Refill Set. https://web.archive.org/web/20160326190615/http://www.truenu.com/TR/Shiseido-Super-Mild-Hair-Care-Shampoo-Conditioner-Refill-Set-Two-400ml-Refill-Pouches-Details.html. Published Mar. 26, 2016.
Non-Final Office Action for copending U.S. Appl. No. 15/941,916, dated Jun. 24, 2020.
Non-Final Office Action for copending U.S. Appl. No. 15/941,965, dated Jul. 15, 2020.
Third Party Observation for counterpart Application No. EP20160869330, dated Jun. 26, 2020.
Third Party Observation for counterpart Application No. EP20160869326, dated Jul. 2, 2020.
Third Party Observation for counterpart Application No. EP20160869327, dated Jul. 2, 2020.
Non-Final Office Action for copending U.S. Appl. No. 16/234,883, dated Aug. 26, 2020.
Mascolo Group, label.m Anti-Frizz Mist, Mintel GNPD, record ID5618119, published Apr. 2018, p. 1-5.
Federici Brands, Color WOW Dream Coat Supernatural Spray, MINTEL GNPD, record ID5637153, published Apr. 2018, p. 1-2.
Garnier, Garnier Fructis Sleek & Shine Moroccan Sleek Oil Treatment, MINTEL GNPD, record ID1876023, published Sep. 2012, p. 1-2.
Ouai, Leave-In Conditioner, MINTEL GNPD, record ID5781323, published Jun. 2018, p. 1-2.
Redken, Redken Pillow Proof Express Treatment Primer, MINTEL GNPD, record ID5117339, published Sep. 2017, p. 1-4.
Redken, Redken Pillow Proof Express Primer Time-Saving Blowdry Primer with Heat Protection, MINTEL GNPD, record ID6117357, published Nov. 2018, p. 1-2.
Redken, Redken Pillow Proof Time-Saving Blowdry Primer with Heat Protection, MINTEL GNPD, record ID4537755, published Jan. 2017, p. 1-3.
Copending U.S. Appl. No. 16/455,139, "Hair Treatment Compositions and Methods for Treating Hair," filed Jun. 27, 2019.
Non-Final Office Action for copending U.S. Appl. No. 15/778,807, dated Oct. 9, 2020.
Non-Final Office Action for copending U.S. Appl. No. 16/176,350, dated Sep. 30, 2020.
Mintel: "Conditioner," Unilever, XP055576893, Database accession No. 3014885, Mar. 2, 2015.
Olaplex Alleges Patent Infringement by L'OREAL re Hairbond-Building Prior to Colouring, Focus on Pigments, vol. 2017, No. 3, Mar. 31, 2017, p. 7.
Final Office Action for copending U.S. Appl. No. 15/339,035, dated May 2, 2019.
International Preliminary Report on Patentability for counterpart Application No. PCT/US2017/058495, dated May 9, 2019.
Notice of Allowance for copending U.S. Appl. No. 15/778,803, dated Jun. 3, 2019.
Extended European Search Report for counterpart Application No. 16869327.3-1114, dated Jun. 4, 2019.

(56) References Cited

OTHER PUBLICATIONS

Mintel: "Detox 7 Day Cure Purifying Serum," XP055593471, Jeanne Gatineau, Feb. 11, 2013.
Extended European Search Report for counterpart Application No. 16869330.7-1114, dated Jul. 5, 2019.
Extended European Search Report for counterpart Application No. 16869326.5-1114, dated Jun. 26, 2019.
Translation of Mexican Office Action for counterpart Application No. Mx/a/2018/005829, dated Jun. 13, 2019.
Non-Final Office Action for copending U.S. Appl. No. 15/339,035, dated Aug. 20, 2019.
Mexican Office Action for counterpart Application No. Mx/a/2017/013983, dated Jul. 2, 2019.
Notice of Allowance for copending U.S. Appl. No. 16/042,478, dated Sep. 25, 2019.
Non-Final Office Action for copending U.S. Appl. No. 15/778,807, dated Sep. 30, 2019.
Brazilian Office Action for counterpart Application No. BR112017023380-0, dated Oct. 10, 2019.
Brazilian Office Action for counterpart Application No. BR112018010381-0, dated Nov. 25, 2019.
Brazilian Office Action for counterpart Application No. BR112018010357-8, dated Nov. 25, 2019.
Mexican Office Action for counterpart Application No. Mx/a/2018/005829, dated Oct. 5, 2019.
Brazilian Office Action for counterpart Application No. BR112018010344, dated Nov. 25, 2019.
Mexican Office Action for counterpart Application No. Mx/a/2017/013983, dated Dec. 16, 2019.
Japanese Office Action for counterpart Application No. 2018-526844, dated Dec. 23, 2019.
Japanese Office Action for counterpart Application No. 2018-526845, dated Dec. 23, 2019.
Japanese Office Action for counterpart Application No. 2018-546409, dated Dec. 23, 2019.
Brazilian Written Opinion for counterpart Application No. BR112018010341, dated Nov. 25, 2019.
Non-Final Office Action for counterpart Japanese Application No. 2018-546408, dated Jan. 6, 2020.
Mintel: "Tonic," Dr. Kurt Wolff, Dr. Wolff Plantur 39, ID# 3133037, Apr. 2015.
Mintel: "Conditioner," LG Household & Health Care, Beyond Professional, ID# 3240637, Jun. 2015.
Russian Office Action for counterpart Application No. 2018114758/04, dated Dec. 13, 2019.
Translated Notification of Reasons for Refusal for counterpart KR Application No. 10-2018-7017668, dated Jan. 21, 2020.
Translated Office Action for counterpart RU Application No. 2017134681/04(0060925), dated Dec. 30, 2019.
Non-Final Office Action for copending U.S. Appl. No. 15/778,805, dated Feb. 12, 2020.
Final Office Action for copending U.S. Appl. No. 15/778,807, dated Mar. 13, 2020.
Final Office Action for copending U.S. Appl. No. 15/339,035, dated Apr. 10, 2020.
Non-Final Office Action for copending U.S. Appl. No. 16/273,787, dated Apr. 9, 2020.
International Search Report and Written Opinion for counterpart Application No. PCT/US2017/059827, dated Jun. 28, 2018.
"LAMESOFT® PO 65 Datasheet," Retrieved from the internet on Jun. 7, 2018, http://e-applications.basf-ag.de/data/basf-pcan/pds2/pds2-web.nsf.
Non-Final Office Action for copending U.S. Appl. No. 15/356,967, dated May 3, 2017.
Final Office Action for copending U.S. Appl. No. 15/356,967, dated Dec. 4, 2017.
Non-Final Office Action for copending U.S. Appl. No. 15/356,967, dated Aug. 24, 2018.
Final Office Action for copending U.S. Appl. No. 15/356,967, dated Apr. 11, 2019.
Non-Final Office Action for copending U.S. Appl. No. 15/356,967, dated Feb. 21, 2020.
Notice of Allowance for copending U.S. Appl. No. 15/604,152, dated Oct. 2, 2019 (now U.S. Pat. No. 10,561,599).
Non-Final Office Action for copending U.S. Appl. No. 15/604,152, dated Jun. 13, 2019.
Olaplex with relaxers, OLAPLEX™, pp. 1-2, Apr. 11, 2017, https://olaplex.es/olaplex-with-relaxers/.
Relaxers, resource Library, Olaplex Education, pp. 1-2, Apr. 11, 2017, https://help.olaplex.com/detail/relaxers.
Notice of Allowability for copending U.S. Appl. No. 15/604,152, dated Dec. 10, 2019.
International Search Report and Written Opinion for counterpart Application No. PCT/US2018/034366, dated Jul. 25, 2018.
Anonymous: "Curly Hair Conditioner," Mintel, GNPD, XP002782449, 2015, pp. 1-2.
Corrected Notice of Allowability for copending U.S. Appl. No. 15/604,189, dated Dec. 11, 2019 (now U.S. Pat. No. 10,576,307).
Notice of Allowance for copending U.S. Appl. No. 15/604,189, dated Oct. 22, 2019.
Copending U.S. Appl. No. 15/484,625, filed Apr. 11, 2017 (WO 2016/179017).
Copending U.S. Appl. No. 15/484,663, filed Apr. 11, 2017 (WO 2017/091794).
Copending U.S. Appl. No. 15/339,035, filed Oct. 31, 2016 (WO 2018/081399).
International Search Report and Written Opinion for counterpart Application No. PCT/US2016/030172, dated Sep. 19, 2016.
International Search Report and Written Opinion for counterpart Application No. PCT/US2016/063724, dated Feb. 2, 2017.
International Search Report and Written Opinion for counterpart Application No. PCT/US2016/063727, dated Feb. 8, 2017.
International Search Report and Written Opinion for counterpart Application No. PCT/US2016/063732, dated Feb. 6, 2017.
International Search Report and Written Opinion for counterpart Application No. PCT/US2016/063728, dated Feb. 1, 2017.
Mintel: "Abundant Volume Conditioner," Alterna Professional Haircare, Database Record No. 2177147, Sep. 2013.
Mintel: "Hair Colourant," Catzy Hair Colourant, Database Record ID 743114, Jul. 2007, 4 pages.
Mintel: "Combing Cream," Devintex Cosmeticos, Database Record No. 1595490, Jul. 2011.
Mintel: "Combing Cream," Devintex Cosmeticos, Database Record No. 1595658, Jul. 2011.
Mintel: "Conditioner," Devintex Cosmeticos, Database Record No. 1595545, Jul. 2011.
Mintel: "Conditioner," Laperle Haircare, Database Record No. 3645337, Feb. 2016.
Mintel: "Conditioner," Laperle Haircare, Database Record No. 3790215, Feb. 2016.
Mintel: "Conditioner," Liqwd, Database Record No. 1172691, Sep. 2009.
Mintel: "Conditioner," TIGI, Database Record No. 1442418, Nov. 2010.
Mintel: "Conditioner," TIGI International, Database Record No. 1445427, Nov. 2010.
Mintel: "Conditioner," TGI International, Database Record No. 3280151, Jul. 2015.
Mintel, "Masque for Beautiful Color," Oribe Hair Care, Database Record No. 1522953, Mar. 2011.
Mintel: "Moisturizing Conditioner," Frederic Fekkai, Datablase Record No. 1507159, Mar. 2011.
Mintel: "Post-Service Perfector," Redken, Database Record No. 4326453, Nov. 2016.
Mintel: "Step 3-Conditioner," L'OREAL, Database Record No. 4353779, Oct. 2016.
Mintel: "Step 3-Conditioner," L'OREAL, Database Record No. 4609117, Feb. 2017.
International Preliminary Report on Patentability for counterpart Application No. PCT/US2016/30172, dated Jun. 19, 2017.
Petition for Post-Grant Review of U.S. Pat. No. 9,498,419, filed Jan. 31, 2017, with Exhibits.

(56) References Cited

OTHER PUBLICATIONS

Non-Final Office Action for copending U.S. Appl. No. 15/484,625, dated Jun. 21, 2017 (now U.S. Pat. No. 10,231,915).
Final Office Action for copending U.S. Appl. No. 15/484,625, dated Nov. 14, 2017 (now U.S. Pat. No. 10,231,915).
Non-Final Office Action for copending U.S. Appl. No. 15/484,663, dated Jun. 21, 2017 (now U.S. Pat. No. 10,058,494).
Final Office Action for copending U.S. Appl. No. 15/484,663, dated Nov. 28, 2017 (now U.S. Pat. No. 10,058,494).
Non-Final Office Action for copending U.S. Appl. No. 15/339,035, dated Jan. 10, 2018.
International Search Report for counterpart Application No. PCT/US2017/058495, dated Jan. 5, 2018.
Third Party Submission for U.S. Appl. No. 15/484,663, filed Feb. 28, 2018, with attachments.
Pressly, Eric et al., U.S. Appl. No. 61/994,709, filed May 16, 2014 and became publicly available on Nov. 19, 2015.
Estetica: the hairstyling professional magazine, (http://estetica.it/int/a/schwarzkopf-professional-launches-fibreplex), "Schwarzkopf Professional Launches Fibreplex®," published Sep. 23, 2015 reporting that Fibreplex was launched during Sep. 2015.
Fibreplex® No. 1 Product Label.
Fibreplex® No. 1 Material Safety Data Sheet.
International Preliminary Report on Patentability for counterpart Application No. PCT/US2016/063727, dated Jun. 7, 2018.
International Preliminary Report on Patentability for counterpart Application No. PCT/US2016/063732, dated Jun. 7, 2018.
International Preliminary Report on Patentability for counterpart Application No. PCT/US2016/063728, dated Jun. 7, 2018.
Non-Final Office Action for copending U.S. Appl. No. 15/484,625, dated Jun. 20, 2018 (now U.S. Pat. No. 10,231,915).
International Preliminary Report on Patentability for counterpart Application No. PCT/US2016/063724, dated Jun. 7, 2018.
Non-Final Office Action for copending U.S. Appl. No. 15/339,035, dated Oct. 5, 2018.
Notice of Allowance for copending U.S. Appl. No. 15/484,625, dated Oct. 31, 2018.
Bayraktar, V.N., "Organic Acids Concentration in Wine Stocks After Saccharomyces Cerevisiae Fermentation," Biotechnologia Acta, vol. 6, No. 2, Jan. 1, 2013, pp. 97-106.
Supplementary European Search Report for counterpart Application No. EP16789846, dated Oct. 30, 2018.
Communication Pursuant to Rules 70(32) and 70a(2) EC for counterpart Application EP16789846, dated Jan. 23, 2019.
Written Opinion for counterpart Application EP16789846, dated Jan. 23, 2019.
Supplementary Extended Search Report and Written Opinion for counterpart European Application No. 16869324, dated Apr. 25, 2019.
Mintel: "Conditioner," Unilever, XP-55576888, Database accession No. 1419415, Oct. 21, 2010.
Translation of Japanese Office Action for counterpart Application No. 2018-526844, dated Aug. 3, 2020.
Translation of Chinese Office Action for counterpart Application No. 201680079110.9, dated Aug. 11, 2020.
Ruiming, Li, "Hairdressing Technology," China Railway Publishing House, Jun. 30, 2015, pp. 112-113.
Translation of Mexican Office Action for counterpart Application No. MX/a/2018/005829 dated Jul. 13, 2020.
Translation of Russian Office Action for counterpart Application No. 2017134681-04, dated Aug. 17, 2020.
Translation of Chinese Office Action for counterpart Application No. 201680079800.4, dated Aug. 24, 2020.
Search Report for counterpart Chinese Application No. 201680079800.4, dated Aug. 24, 2020.
Translation of Chinese Office Action for counterpart Application No. 201680079773.0, dated Aug. 21, 2020.
Search Report for counterpart Chinese Application No. 201680079773.0, dated Aug. 21, 2020.
Translation of Japanese Office Action for counterpart Application No. 2018-546409, dated Sep. 7, 2020.
Translation of Chinese Office Action for counterpart Application No. 201680079774.5, dated Sep. 1, 2020.
Fridman, R.A., "Technology of Cosmetics," publ. of "Food Industry," 1964, pp. 3-6, 297-308, 411-428 and 441-466 (translation).
Zefirova, N.S., "Big Russian Encyclopedia," Chemical Encylopedia, 1995, vol. 4, pp. 183-185 (translation).
Third Party Submission for U.S. Appl. No. 16/712,326 with attachments, filed Sep. 8, 2020.
Mexican Office Action for counterpart Application No. MX/a/2017/013983, dated Sep. 15, 2020.
Japanese Notice of Reasons for Refusal for counterpart Application No. 2019-553190, dated Oct. 27, 2020.
Translation of Korean Notice of Last Preliminary Rejection for counterpart Application No. 10-2018-7017668, dated Jan. 21, 2020.
Translation of Japanese Office Action for counterpart Application No. 2018-546408, dated Dec. 7, 2020.
Translation of Japanese Notice of Reasons for Rejection for counterpart Application No. 2019-553559, dated Dec. 1, 2020.
Translation of Notice of Reasons for Rejection for counterpart Application No. 2019-564945, dated Dec. 1, 2020.
Translation of Third Party Observation for Application No. 2018-546408, dated Sep. 11, 2020.
European Office Action for counterpart Application No. 16869327.3-1112, dated Dec. 18, 2020.
Non-Final Office Action for copending U.S. Appl. No. 15/942,042, dated Nov. 12, 2020.
Final Office Action for copending U.S. Appl. No. 15/357,056, dated Nov. 19, 2020.
Final Office Action for copending U.S. Appl. No. 16/234,883, dated Dec. 24, 2020.
Non-Final Office Action for copending U.S. Appl. No. 16/455,139, dated Jan. 26, 2021.
Final Office Action for copending U.S. Appl. No. 15/941,916, dated Mar. 10, 2021.
Translation of Russian Office Action for counterpart Application No. 2018114758/04, dated Dec. 21, 2020.
Translation of Chinese Office Action for counterpart Application No. 201680039105.5, dated Feb. 4, 2021.
European Office Action for counterpart Application No. 16869330.7-1112, dated Feb. 4, 2021.
European Office Action for counterpart Application No. 16869324.0-1112, dated Feb. 18, 2021.
Translation of Chinese Office Action for counterpart Application No. 201680079800.4, dated Feb. 24, 2021.
Supplemental Search Report for Chinese counterpart Application No. 201680079800.4, dated Feb. 18, 2021.
Chinese Office Action for counterpart Application No. 201880021603.6, dated Mar. 2, 2021.
International Search Report dated Feb. 6, 2018 in corresponding PCT Application No. PCT/US17/59817.
Partial Translation of Office Action for counterpart MX Application No. MX/a/2017/013983, dated Apr. 4, 2021.
Translation of Chinese Office Action for counterpart Application No. 201680079773, dated Apr. 14, 2021.
Translation of Japanese Office Action for counterpart Application No. 2017-557074, dated May 31, 2021.
Final Office Action for copending U.S. Appl. No. 15/941,965, dated Apr. 5, 2021.
Final Office Action for copending U.S. Appl. No. 15/942,042, dated May 12, 2021.
Non-Final Office Action for copending U.S. Appl. No. 15/942,085, dated Jun. 8, 2021.
"Oxy Cream," Makki Cosmetics, https://www.makkicosmetics.com/makk/showProductjsp?productID=Oxy25030&brandID=Makki, published Jun. 30, 2016.
Shoup, F.K , et al., "Amino Acid Composition of Wheat Varieties and Flours Varying Widely in Bread-Making Potentialities," Journal of Food Science, vol. 31, Issue 1, published Jan. 1966, pp. 94-101.
Tetrasodium Etidronate, https://uk.lush.com/ingredients/tetrasodium-etidronate. Published Mar. 28, 2020.

(56) References Cited

OTHER PUBLICATIONS

Translation of Japanese Notice of Reasons for Refusal for counterpart Application No. 2019-553190, dated Jun. 12, 2021.
Non-Final Office Action for copending U.S. Appl. No. 15/339,035, dated Jun. 25, 2021.
Non-Final Office Action for copending U.S. Appl. No. 15/603,889, dated Jun. 25, 2021.
Final Office Action for copending U.S. Appl. No. 15/778,807, dated Jul. 21, 2021.
Non-Final Office Action for copending U.S. Appl. No. 15/356,967, dated Jul. 22, 2021.

* cited by examiner

COMPOSITIONS AND METHODS FOR IMPROVING THE QUALITY OF CHEMICALLY TREATED HAIR

FIELD OF THE DISCLOSURE

The present disclosure relates to compositions and methods for chemically treating hair, kits comprising the compositions, and methods for using the compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening (or bleaching), generally requires the use of oxidizing agents. Lightening of hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels can range from 1 (black) to 10 (light blond), one unit corresponding to one tone; thus, the higher the number, the lighter the shade or the greater the degree of lift.

In general, hair lightening or color lifting compositions and hair coloring or dyeing compositions possess an alkalinity such that these compositions have a pH value of above 7, typically being at pH 9 and above, and may generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effective alter the shape of the hair, these chemical treatments can damage the hair fibers and/or irritate the scalp. Thus, in order to reduce or avoid damage to hair, as well as to improve the cosmetic performance of the compositions, the use of new and additional components and novel combinations of ingredients are continuously sought.

However, the choice of components or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can chemically treat the hair while providing other cosmetic advantages such as shine, conditioning, fiber strength, and/or a healthy appearance to the hair, but avoiding or minimizing damage to the hair.

Further, both natural and sensitized or chemically treated hair can contain several kinds of negatively charged moieties, for example, carboxylates (resulting from the hydrolysis of amino acids and thioester bonds) and/or sulfonates (resulting from the oxidation of disulfide bonds). These negatively charged moieties can degrade the cosmetic properties of the hair. Moreover, when hair is chemically treated or damaged, the disulfide bonds in hair (disulfide linkages between two cysteine units) can be reduced or broken, resulting in the formation of thiol groups and/or cysteic acid.

Thus, one objective of the disclosure is to provide novel compositions that can provide advantageous effects such as strengthening of the hair fiber, protecting hair fibers from damage or further damage, enhanced properties such as softness, shine, conditioning, healthy appearance, while at the same time, providing desired effects such as coloring, lightening, straightening, relaxing, and/or shaping.

SUMMARY OF THE DISCLOSURE

The present disclosure relates to compositions, kits, and methods for chemically treating hair, in particular human hair of the head. The compositions and methods are unique because they dramatically improve the quality of the chemically treated hair. Damage during chemical treatment is mitigated and the hair exhibits dramatically improved softness, smoothness, and discipline.

The compositions include one or more polymeric acid compounds and/or polymeric acid anhydride compounds in addition to one or more active agents that chemically treat the hair. Also, the compositions may optionally include one or more non-polymeric, mono-, di-, and/or tri-carboxylic acids; and may optionally include one or more mono- and/or di-amines.

The active agents for chemically treating the hair may be, for example, oxidizing agents, reducing agents, non-reducing agents for shaping hair, dyeing agents, and mixtures thereof. Depending on the type of active agent(s), the composition may be, for example, a hair lightening or bleaching composition, a hair coloring or dyeing composition, or a hair perming or straightening composition.

The instant disclosure also relates to methods for chemically treating hair. The compositions are applied to the hair and allowed to remain on the hair for a period of time sufficient to achieve a desired result. Typically, a composition is allowed to remain on the hair for about 1 min. to about 45 min. and then the composition is rinsed from the hair. The methods do not require the use of heat. Accordingly, the methods may be carried out at room temperature (about 20° C. to about 30° C.) or at a temperature of about 10° C. to about 50° C.

Also described are methods for treating hair, wherein the one or more polymeric acid compounds and/or polymeric acid anhydride compounds and the one or more active agents are in different compositions that are sequentially applied to the hair. The separate compositions are typically sequentially applied to the hair a period of about 2 hours. These methods also do not require the use of heat. Therefore, the method may be carried out at room temperature (e.g., from about 20° C. to about 30° C.) or at a temperature of about 10° C. to about 50° C.

Finally, the instant disclosure relates to kits comprising the compositions described herein. For example, a kit may include a composition comprising one or more polymeric acid compounds and/or polymeric acid anhydride compounds and one or more active agents for chemically treating the hair; and optionally a second composition comprising one or more second active ingredients. Also, in some cases, the kit may include a composition comprising one or more polymeric acid compounds and/or polymeric acid anhydride compounds, and separately a composition comprising one or more active agents. The kit may also optionally include additional compositions, for example a composition comprising one or more second active agents.

DETAILED DESCRIPTION OF THE DISCLOSURE

Hair chemically treated with compositions, kits, and methods according to the instant disclosure exhibits dramatic improvements in softness, smoothness, and discipline. The compositions typically include: (a) one or more polymeric acid compounds and/or polymeric acid anhydride compounds; and (b) one or more active agents. The one or more polymeric acid compounds and/or polymeric acid anhydride compounds has recurring units. The recurring units may be derived from one more of the following acids (or anhydrides, salts, or derivatives of the acids):
  (i) styrene sulfonic acid,
  (ii) crotonic acid,
  (iii) acrylic or methacrylic acid,
  (iv) ethylene-$\alpha,\beta$-dicarboxylic acid, and/or
  (v) allyloxyacetic acid, methallyloxyacetic acid, 3-allyloxypropionic acid, allylthioacetic acid, allylaminoacetic acid, vinylacetic acid, vinyloxyacetic acid, crotyloxyacetic acid, 3-butenoic acid, 4-pentenoic acid, 10-undecenoic acid, allylmalonic acid, maleamic acid, itaconamic acid or N-monohydroxyalkyl- or N-dihydroxy-alkyl-maleamic or -itaconamic acids.

In some cases, the one or more polymeric acid compounds and/or polymeric acid anhydride compounds are ethylene-$\alpha,\beta$-dicarboxylic acids, anhydrides, salts, or derivatives thereof. Suitable $\alpha,\beta$-unsaturated carboxylic acids for copolymerization with ethylene are $\alpha,\beta$-unsaturated aliphatic mono- or di-carboxylic acids having 3 to 8 or 3 to 5 carbon atoms. Non-limiting examples include acrylic acid, methacrylic acid, $\alpha$-ethylmethacrylic acid, maleic acid, fumaric acid, and itaconic acid anhydrides, salts, or derivatives thereof. In some instances in particular, maleic acid, anhydrides, salts, or derivatives thereof are appropriate. Accordingly, the instant disclosure relates to compositions that include: (a) one or more polymers containing recurring units derived from maleic acid and/or maleic anhydride; and (b) one or more active agents.

Non-limiting examples of polymeric acid compounds and/or polymeric acid anhydride compounds include maleic anhydride copolymers such as poly(styrene-alt-maleic anhydride), poly(methyl vinyl ether-alt-maleic anhydride), poly(ethylene-g-maleic anhydride), poly(isobutylene-alt-maleic anhydride), polyisoprene-g-maleic anhydride, poly(maleic anhydride-alt-1-octadecene), poly(ethylene-co-ethyl acrylate-co-maleic anhydride), polyethylene-graft-maleic anhydride, and mixtures thereof.

Further non-limiting examples of polymeric acid compounds and/or polymeric acid anhydride compounds include maleic acid copolymers such as butyl ester of ethylene/MA copolymer, butyl ester of PVM/MA copolymer, calcium/sodium salt of PVM/MA copolymer, ethyl ester of PVM/MA copolymer, ethylene/MA copolymer, isobutylene/MA copolymer, isopropyl ester of PVM/MA copolymer, octadecene/MA copolymer, polyethylene/isopropyl maleate/MA copolymer, polyvinyl methyl ether (PVM)/MA copolymer, PVM/MA decadiene crosspolymer, sodium C4-C12 olein/maleic acid copolymer, sodium isooctylene/MA copolymer, sodium MA/diisobutylene copolymer, sodium PVM/MA/decadiene crosspolymer, stearylvinyl ether/MA copolymer, styrene/MA copolymer, and mixtures thereof.

The total amount of the polymeric acid compounds and/or polymeric acid anhydride compounds may vary. For example, in some cases the total amount is about 0.01 to about 25 wt. %, based on the total weight of the composition. However, the total amount of the one or more polymeric acid compounds and/or polymeric acid anhydride compounds may be about 0.01 to about 20 wt. %, about 0.01 to about 15 wt. %, about 0.01 to about 10 wt. %, about 0.01 to about 8 wt. %, 0.01 to about 5 wt. %, about 0.01 to about 4 wt. %, about 0.01 to about 3 wt. %, about 0.1 to about 10 wt. %, about 0.1 to about 8 wt. %, about 01 to about 5 wt. %, about 0.1 to about 4 wt. %, or about 0.1 to about 3 wt. %.

An "active agent," in the context of the instant disclosure, relates to a compound, molecule, or combination of compounds/molecules that chemically changes hair. For example, an active agent may reduce disulfide bonds, reestablish or form disulfide bonds, remove melanin from the hair, covalently bond to the hair, etc. Non-limiting examples of active agents include oxidizing agents, reducing agents, non-reducing agents for shaping hair, dyeing agents, and mixtures thereof. Based on the type of active agent, the composition for chemically treating hair may be a hair lightening or bleaching composition, hair coloring composition, a hair perming or straightening composition, or a mixture thereof.

Hair lightening compositions typically include one or more oxidizing agents. Non-limiting examples of oxidizing agents include peroxides, persulfates, perborates, percarbonates, and mixtures thereof. In some cases, the hair lightening composition includes one or more persulfates, such as those selected from the group consisting of sodium persulfate, potassium persulfate, ammonium persulfate, and mixtures thereof. In some cases, the hair lightening compositions include peroxide, such as hydrogen peroxide.

Hair perming or straightening compositions typically include one or more reducing agents. Non-limiting examples of reducing agents include cysteine or a derivative of cysteine, cysteamine or a derivative of cysteamine, thiolactic acid or an ester of thiolactic acid, thioglycolic acid or an ester of thioglycolic acid, thioglycerol, and mixtures thereof. In some cases, the reducing agent is a glyceryl or glycol monothioglycolate, diammonium dithiodiglycolate, ammonium thioglycolate, or a mixture thereof.

Hair straightening or relaxing compositions may include one or more non-reducing agents for shaping hair. Non-reducing agents for shaping hair may be one or more hydroxide compounds, non-hydroxide compounds, or mixtures thereof. For instance, the hydroxide compounds may be alkali metal hydroxides, alkaline-earth metal hydroxides, transition metal hydroxides, and mixtures thereof. Non-limiting examples include of hydroxide compounds include sodium hydroxide, potassium hydroxide, lithium hydroxide, calcium hydroxide, magnesium hydroxide, barium hydroxide, strontium hydroxide, manganese hydroxide, zinc hydroxide, guanidine hydroxide, and mixtures thereof.

The non-hydroxide compounds may include one or more ethyleneamines, alkanolamines, amino acids, or mixtures thereof. Non-limiting examples of non-hydroxide compounds include ethylenediamine, monoethanolamine, diethanolamine, propanolamine, isopropanolamine, triethanolamine, butanolamine, isobutanolamine, methylethanolamine, butylethanolamine, arginine, lysine, and mixtures thereof.

In some cases, when the compositions include hydrogen peroxide as an active agent, the composition further comprises a second oxidizing agent other than hydrogen peroxide and/or the compositions includes an oxidative dye precursor. For example, in some cases the second oxidizing agent is a persulfate. Non-limiting examples of persulfates include potassium persulfate, sodium persulfate, ammonium persulfate, and mixtures thereof.

Hair coloring or dyeing compositions typically include one or more colorants or dyeing agents. Non-limiting examples of colorants or dyeing agents include direct dyes, oxidative dyes, direct action dyes, natural dyes, metallic dyes, reactive dyes, and mixtures thereof.

In addition to the (a) one or more polymeric acid compounds and/or polymeric acid anhydride compounds and (b) one or more active agents, the compositions may also optionally include (c) one or more non-polymeric, mono-, di-, and/or tri-carboxylic acids; and may optionally include (d) one or more mono-amines, di-amines, and/or polyamines having more than 2 amino groups.

Non-limiting examples of mono-carboxylic acids include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, and mixtures thereof.

Non-limiting examples of di-carboxylic acids include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, and mixtures thereof.

Non-limiting examples of tri-carboxylic acids include citric acid, isocitric acid, aconitric acid, propane-1,2,3-tricarboxylic acid, benzene-1,3,5-tricarboxylic acid, and mixtures thereof.

In some cases, the compositions include one or more di-carboxylic acids, such as those set forth above. Additionally, in some instances, the compositions include a di-carboxylic acid selected from the group consisting of maleic acid, malonic acid, and mixtures thereof; and in some cases, the compositions include at least maleic acid.

The total amount of the one or more mono-, di-, and/or tri-carboxylic acids may vary but in some instances, the total amount is about 1 to about 50 wt. %, based on the total weight of the composition. In some cases, the total amount of the one or more mono-, di-, and/or tri-carboxylic acids, if present, is about 1 to about 40 wt. %, about 1 to about 30 wt. %, about 1 to about 25 wt. %, about 1 to about 20 wt. %, about 5 to about 50 wt. %, about 5 to about 40 wt. %, about 5 to about 30 wt. %, about 5 to about 25 wt. %, or about 5 to about 20 wt. %.

The one or more monoamines and/or diamines may be primary, secondary, or tertiary amines, or mixtures thereof. For instance, the monoamines and diamines may be alkyl amines, amidoamines, amino silicones, alkoxylated monoamines, and mixtures thereof. Non-limiting examples include aminosilicones, polyvinylamines, aminated polysaccharides, amine substituted polyalkylene glycols, amine substituted polyacrylate crosspolymers, amine substituted polyacrylates, amine substituted polymethacrylates, proteins, protein derivatives, amine substituted polyesters, polyamino acids, polyalkylamines, diethylene triamine, triethylenetetramine, spermidine, spermine and mixtures thereof. In some cases, the composition includes one or more monoamines selected from the group consisting of monoethanolamine, propanolamine, isopropanolamine, triethanolamine, butanolamine, isobutanolamine, methylethanolamine, butylethanolamine, and mixtures thereof.

Non-limiting examples of diamines include ethylenediamine (1,2-diaminoethane), 1,3-diaminopropane (propane-1,3-diamine), putrescine (butane-1,4-diamine), cadaverine (pentane-1,5-diamine), hexamethylenediamine (hexane-1,6-diamine), 1,2-diaminopropane, diphenylethylenediamine, diaminocyclohexane, xylylenediamine (o-xylylenediamine, m-xylylenediamine, and p-xylylenediamine), phenylenediamine (o-phenylenediamine, m-phenylenediamine, p-phenylenediamine), 2,5-diaminotoluene, dimethyl-4-phenylenediamine, N,N'-di-2-butyl-1,4-phenylenediamine, 4,4'-diaminobiphenyl, 1,8-diaminonaphthalene, and mixtures thereof.

Polyamines have more than 2 amino groups and may be a polymer comprising multiple amino groups including homopolymers, copolymers, and terpolymers. For instance, the polyamine may be an alkoxylated polyamine having at least two amino groups and at least one degree of alkoxylation. The alkoxylation is provided by an alkylene oxide group such as, for example, ethylene oxide and/or propylene oxide. In some cases, the compositions do not include polymers having dimethylamino moieties, i.e., the compositions are free of essentially free of polyamines that are polymers having dimethylamino moieties.

In some instances, the compositions of the instant disclosure are free or essentially free of VP/DMAPA acrylates copolymer. VP/DMAPA acrylates copolymer is a copolymer of vinylpyrrolidone and dimethylaminopropylacrylamide or methacrylamide. In some cases, when the compositions of the instant disclosure include an oxidizing agent, the compositions are free or essentially free of VP/DMAPA acrylates copolymer. In some cases, when the compositions of the instant disclosure include hydrogen peroxide, the compositions are free or essentially free of VP/DMAPA acrylates copolymer. Furthermore, individual polyamines that may be include or excluded from the instant compositions include include polyethyleneimines, polyvinylamines, aminated polysaccharides, amine substituted polyalkylene glycols, amine substituted polyacrylate crosspolymers, amine substituted polyacrylates, amine substituted polymethacrylates, amine substituted polyesters, polyamino acids, polyalkylamines, diethylene triamines, triethylenetetramines, and mixtures thereof. Polyimide-1 may also optionally be included or excluded, or present in an amount less than about 5 wt. %, about 4 wt. %, about 3 wt. %, about 2 wt. %, about 1 wt. %, about 0.5 wt. %, about 0.1 wt. %, about 0.05 wt. % or about 0.01 wt. %.

The total amount of the one or more mono-amines, di-amines, and/or polyamines may vary, but in some cases, the total amount is about 0.1 to about 35 wt. %, based on the total weight of the composition. In some cases, the total amount is about 0.1 to about 30 wt. %, about 0.1 to about 25 wt. %, about 0.1 to about 20 wt. %, about 0.1 to about 15 wt. %, about 0.1 to about 10 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, or about 3 to about 8 wt. %.

The instant disclosure also relates to methods for chemically treating hair using compositions described above. For example, the methods may include applying to the hair a composition for chemically treating the hair comprising one or more polymeric acid compounds and/or polymeric acid anhydride compounds and one or more agents for chemically treating the hair. The compositions optionally include one or more non-polymeric, mono-, di-, and/or tri-carboxylic acids; and optionally include one or more mono-amines, di-amines, and/or polyamines having more than 2 amino groups.

Depending on the type of active agent(s), the disclosure relates to methods for lightening or bleaching hair, methods for altering the color of hair, methods for coloring or dyeing the hair, methods for perming hair, methods for straightening hair, methods for reducing hair frizz, methods for conditioning hair, methods for improving the quality of the chemically treated hair, and methods for improving the softness, smoothness, and discipline of hair.

In some methods, the one or more polymeric acid compounds and/or polymeric acid anhydride compounds are in a separate composition than the one or more active agents and the methods include: (i) applying to the hair a composition comprising one or more polymeric acid compounds and/or polymeric acid anhydride compounds; and (ii) applying to the hair a composition comprising one or more active agents. One or both of the compositions may optionally include one or more non-polymeric, mono-, di-, and/or tri-carboxylic acids; and may optionally include one or more mono- and/or di-amines. When the one or more polymeric acid compounds and/or polymeric acid anhydride compounds are in separate compositions, the compositions are typically sequentially applied to the hair within a 24 hour period. In some cases, the compositions are applied to the hair within a 10 hour period, a 4 hour period, a 2 hour period, a 1 hour period, or a 30 min. period. The composition comprising the one or more polymeric acid compounds and/or polymeric acid anhydride compounds may be applied first and the composition comprising the one or more active agents may be applied second. In some cases the order is reversed. The composition comprising the one or more active agents is applied first followed by application of the composition comprising the one or more polymeric acid compounds and/or polymeric acid anhydride compounds. The sequential application of these compositions can be carried out repeatedly, for example, the sequential application can be carried out 1, 2, 3, 4, 5 or more times within a period of 24 hours.

The compositions described above are typically allowed to remain on the hair for a period of time sufficient to achieve a desired result, and then rinsed from the hair. The compositions may be applied to the hair for about 1 min. to about 1 hour, about 1 min. to about 45 min., about 1 min. to about 30 min., about 1 min. and about 20 min., about 1 min. to about 15 min., about 10 min., or about 5 min., and then rinsed from the hair.

The methods are unique because they do not require heat to attain the dramatic improvements in cosmetic and/or sensorial properties (e.g., softness, smoothness, discipline, conditioning, etc.). Thus, the methods are typically carried out at room temperature (about 20° C. to about 30° C.). In particular, methods can be performed without allowing the hair and the compositions applied to the hair to reach a temperate above about 50° C. or about 60° C. The methods can be performed without applying heat during treatment or after treatment. Accordingly, the methods may be carried out at a temperature of about 10° C. to about 60° C., about 15° C. to about 50° C., about 15° C. to about 40° C., or about 15° C. to about 30° C.

Finally, the instant disclosure relates to kits comprising the compositions described herein. For example, a kit may include a composition comprising one or more more polymeric acid compounds and/or polymeric acid anhydride compounds and one or more active agents for chemically treating the hair; and optionally a second composition comprising one or more second active ingredients. Also, in some cases, the kit may include a composition comprising one or more more polymeric acid compounds and/or polymeric acid anhydride compounds, and separately a composition comprising one or more active agents. The kit may also optionally include additional compositions, for example a composition comprising one or more second active agents; or a compositions comprising one or more conditioning agent (or polymers) or one or more coloring agents (or dyes).

Preservatives, conditioning agents including cationic conditioning agents, thickeners, surfactants including ionic surfactants, nonionic surfactants, amphoteric surfactants and/or zwitterionic surfactants, stabilizers, pH modifiers, buffers, etc., may also optionally be included (or excluded) from the compositions.

More exhaustive but non-limiting lists of components that may be useful in the compositions of the instant disclosure are presented below.

Polymeric Acid and Polymeric Acid Anhydride Compounds

The polymeric acid and polymeric acid anhydride compounds of the present disclosure are polymers derived from at least one of carboxylics acid, sulfonic acids, and phosphoric acids, and generally have a number-average molecular mass ranging from 500 to 5,000,000.

The polymeric acid and polymeric acid anhydride compounds may be chosen from aliphatic, cycloaliphatic and aromatic polyacids, unsaturated polyacids, and associative polyacids. The carboxylic groups may be provided, for example, by unsaturated monocarboxylic or dicarboxylic acid monomers such as those corresponding to the following formula:

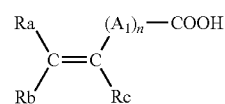

in which: n is an integer ranging from 0 to 10, $A_1$ is chosen from methylene groups, optionally connected to the carbon atom of the unsaturated group, or to the neighboring methylene group when n is greater than 1, via a hetero atom such as oxygen and sulfur, $R_a$ is chosen from hydrogen phenyl groups, and benzyl groups, $R_b$ is chosen from hydrogen, $(C_{1-4})$alkyl groups, for example, methyl and ethyl, and carboxyl groups, and $R_c$ is chosen from hydrogen, lower alkyl groups, —CH2—COOH groups, phenyl groups, and benzyl groups.

Suitable polymers comprising carboxylic groups include, for example:

A) acrylic or methacrylic acid homo- and copolymers, and salts thereof, for example, the products sold under the names VERSICOL E and K by Allied Colloid and Ultrahold by BASF, copolymers of acrylic acid and of acrylamide, and sodium salts of polyhydroxycarboxylic acid;

B) copolymers of acrylic or methacrylic acid with a monoethylenic monomer such as ethylene, styrene, vinyl esters, acrylic or methacrylic acid esters, optionally grafted onto a polyalkylene glycol such as polyethylene glycol and optionally crosslinked. Such polymers are described, for example, in French Patent No. 1 222 944 and German Patent Application No. 2 330 956, the copolymers of this type comprising an optionally N-alkylated and/or hydroxyalkylated acrylamide unit in their chain as described, for example, in Luxembourg Patent Application Nos. 75370 and 75371. Other examples include copolymers of acrylic acid and of C1-C4 alkyl methacrylate and terpolymers of vinylpyrrolidone, of acrylic acid and of methacrylate of C1-C20 alkyl, for example of lauryl, such as the product sold by ISP under the name ACRYLIDONE LM and methacrylic acid/ethyl acrylate/tert-butyl acrylate terpolymers such as the product sold under the name LUVIMER 100 P by BASF;

C) copolymers derived from crotonic acid such as those comprising vinyl acetate or propionate units in their chain and optionally other monomers such as allylic esters or methallylic esters, vinyl ether or vinyl ester of a linear or branched saturated carboxylic acid with a long hydrocarbon-based chain such as those comprising at least 5 carbon atoms, it being possible for these polymers optionally to be grafted and crosslinked, or alternatively another vinyl, allylic or methallylic ester monomer of an alpha- or beta-cyclic carboxylic acid. Such polymers are described, for example, in French Patent Nos. 1 222 944, 1 580 545, 2 265 782, 2 265 781, 1 564 110, and 2 439 798. A non-limiting example of a suitable commercial product is the resin 28-29-30 sold by National Starch;

D) copolymers derived from C4-C8 monounsaturated carboxylic acids chosen from: copolymers comprising (i) at least one entity chosen from maleic, fumaric, and itaconic acids and anhydrides and (ii) at least one monomer chosen from vinyl esters, vinyl ethers, vinyl halides, phenylvinyl derivatives, and acrylic acid and its esters, the acid functions of these copolymers optionally being monoesterified or monoamidated. Such polymers are described, for example, in U.S. Pat. Nos. 2,047,398, 2,723,248, and 2,102,113 and British Patent No. 839 805. Suitable commercial products include, for example, those sold under the names GANTREZ S and ES by ISP, copolymers comprising (i) at least one unit chosen from maleic, citraconic, and itaconic acid units and (ii) at least one monomer chosen from allylic or methallylic esters optionally comprising at least one group chosen from acrylamide, methacrylamide, and alpha-olefin groups, acrylic esters, methacrylic esters, acrylic acids, methacrylic acids, and vinylpyrrolidone in their chain, the acid functions of these copolymers optionally being monoesterified or monoamidated. These polymers are described, for example, in French Patent Nos. 2 350 384 and 2 357 241;

E) polyacrylamides comprising carboxylate groups; and

F) anionic polyurethanes, such as the product sold by BASF under the name LUVISET PUR.

The polymeric acid and polymeric acid anhydride compounds comprising sulfonic groups may be polymers comprising vinylsulfonic, styrenesulfonic, naphthalenesulfonic, and/or acrylamidoalkylsulfonic units. These polymers may be chosen, for example, from: polyvinylsulfonic acid salts having a molecular weight ranging from 1000 to 100,000, as well as copolymers with an unsaturated comonomer such as acrylic or methacrylic acids and their esters, as well as acrylamide and its derivatives, vinyl ethers, and vinylpyrrolidone;

polystyrenesulfonic acid salts, such as the sodium salts sold, for example, under the name FLEXAN 130 by National Starch. These compounds are described, for example, in French Patent No. 2 198 719; polyacrylamidesulfonic acid salts, such as those mentioned in U.S. Pat. No. 4,128,631, for example, polyacrylamidoethylpropanesulfonic acid.

The polymeric acid and polymeric acid anhydride compounds may be chosen from those of grafted silicone type comprising a polysiloxane portion and a portion consisting of a non-silicone organic chain, one of the two portions constituting the main chain of the polymer, the other being grafted onto the said main chain. These polymers are described, for example, in European Patent Application Nos. 0 412 704, 0 412 707, 0 640 105, and 0 582 152, International Patent Application Publication Nos. WO 95/00578 and WO 93/23009, and U.S. Pat. Nos. 4,693,935, 4,728,571, and 4,972,037. Such polymers may include, for example, copolymers that can be obtained by radical polymerization from a monomer mixture comprising:

a) 50 to 90 percent by weight of tert-butyl acrylate;
b) 0 to 40 percent by weight of acrylic acid; c) 5 to 40 percent by weight of silicone macromer of formula (II):

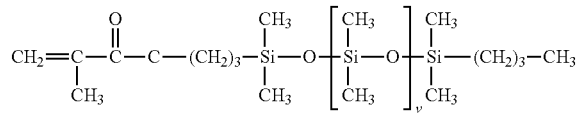

with v being a number from 5 to 700; the weight percentages being calculated relative to the total weight of the monomers.

Other examples of grafted silicone polymers include, but are not limited to, polydimethylsiloxanes (PDMSs) onto which are grafted, via a thiopropylene-type connecting chain, mixed polymer units of the poly(meth)acrylic acid type and of the polyalkyl (meth)acrylate type and polydimethylsiloxanes (PDMSs) onto which are grafted, via a thiopropylene-type connecting chain, polymer units of the polyisobutyl (meth)acrylate type.

In some cases, functionalized silicone or non-silicone polyurethanes may also be used as film-forming polymers. Examples of suitable polyurethanes include those disclosed in European Patent Nos. 0 751 162, 0 637 600, 0 648 485, 0 619 111, and 0 656 021, French Patent No. 2 743 297, and International Patent Application Publication No. WO 94/03510.

Also, the polymers may be chosen from acrylic acid copolymers, such as the acrylic acid/ethyl acrylate/N-tert-butylacrylamide terpolymers sold under the name ULTRAHOLD Strong by BASF, copolymers derived from crotonic acid, such as vinyl acetate/vinyl tert-butylbenzoate/crotonic acid terpolymers and the crotonic acid/vinyl acetate/vinyl neododecanoate terpolymers sold under the name Resin 28-29-30 by National Starch, polymers derived from maleic, fumaric, or itaconic acids with isobutylene, vinyl esters, vinyl ethers, vinyl halides, phenylvinyl derivatives and acrylic acid and esters thereof, such as the methyl vinyl ether/monoesterified maleic acid copolymers sold, for example, under the name GANTREZ by ISP, the copolymers of methacrylic acid and of methyl methacrylate sold under the name EUDRAGIT L by Rohm Pharma, the copolymers of methacrylic acid and of ethyl acrylate sold under the name LUVIMER MAEX and MAE by BASF, the vinyl acetate/crotonic acid copolymers and the vinyl acetate/crotonic acid copolymers grafted with polyethylene glycol sold under the name ARISTOFLEX A by BASF, and the polyurethane LUVISET PUR sold by BASF.

The polymers may, in at least some cases, be chosen from the methyl vinyl ether/monoesterified maleic acid copolymers sold under the name GANTREZ ES 425 by ISP, the acrylic acid/ethyl acrylate/N-tert-butylacrylamide terpolymers sold under the name ULTRAHOLD Strong by BASF, the copolymers of methacrylic acid and of methyl methacrylate sold under the name EUDRAGIT L by Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by National Starch, the copolymers of methacrylic acid and of ethyl acrylate sold under the name LUVIMER MAEX and MAE by BASF, the vinylpyrrolidone/acrylic acid/lauryl methacrylate terpolymers sold under the name ACRYLIDONE LM by ISP, and the polyurethane LUVISET PUR sold by BASF.

The polymeric acid and polymeric acid anhydride compounds of the present disclosure may also include, for example, those polymers comprising units B and C distributed randomly in the polymer chain, in which B denotes a unit derived from a monomer comprising at least one basic nitrogen atom and C denotes a unit derived from an acid monomer comprising at least one group chosen from carboxylic and sulfonic groups, or alternatively B and C may denote groups derived from monomers chosen from carboxybetaine and sulfobetaine zwitterionic monomers.

B and C may also denote a cationic polymer chain comprising primary, secondary, tertiary, and/or quaternary amine groups, in which at least one of the amine groups bears a carboxylic or sulfonic group connected via a hydrocarbon-based group or alternatively B and C form part of a chain of a polymer containing an alpha-dicarboxylic ethylene unit in which one of the carboxylic groups has been made to react with a polyamine containing one or more primary or secondary amine groups.

Non-limiting examples of polymers corresponding to the definition given above include:

(1) polymers resulting from the copolymerization of a monomer derived from a vinyl compound comprising a carboxylic group such as acrylic acid, methacrylic acid, maleic acid, and alpha-chloroacrylic acid, and a basic monomer derived from a substituted vinyl compound comprising at least one basic atom (for example, an amino function), such as dialkylaminoalkyl methacrylate and acrylate, and dialkylaminoalkylmethacrylamides and dialkylaminoalkylacrylamides. Such compounds are described, for example, in U.S. Pat. No. 3,836,537. A non-limiting example of a commercially available product is the sodium acrylate/acrylamidopropyl trimethylammonium chloride copolymer sold under the name POLYQUART KE 3033 by Henkel.

The vinyl compound may also be a dialkyldiallylammonium salt such as diethyldiallylammonium chloride. The copolymers of acrylic acid and of the latter monomer are sold, for example, under the names MERQUAT 280, MERQUAT 295, and MERQUAT Plus 3330 by Calgon.

(2) polymers comprising units derived from: a) at least one monomer chosen from acrylamides and methacrylamides substituted on the nitrogen atom with an alkyl group, b) at least one acidic comonomer comprising at least one reactive carboxylic group, and c) at least one basic comonomer such as esters containing primary, secondary, tertiary, and quaternary amine substituents of acrylic and methacrylic acids and the product of quaternization of dimethylaminoethyl methacrylate with dimethyl or diethyl sulfate.

The N-substituted acrylamides or methacrylamides may include compounds in which the alkyl groups comprise from 2 to 12 carbon atoms, for example, N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers may be chosen, for example, from acrylic acid, methacrylic acid, crotonic acid, itaconic acid, maleic acid, fumaric acid, and alkyl monoesters, comprising from 1 to 4 carbon atoms, of maleic or fumaric acids and anhydrides. Suitable basic comonomers include, for example, aminoethyl, butylaminoethyl, N,N'-dimethylaminoethyl, and N-tert-butylaminoethyl methacrylates. A further non-limiting example is the copolymer whose CTFA (4th edition, 1991) name is octylacrylamide/acrylates/butylaminoethyl methacrylate copolymer, such as the products sold under the names AMPHOMER and LOVOCRYL 47 by National Starch.

(3) crosslinked and acylated polyamino amides partially or totally derived from polyamino amides of the following formula:

$$CO-R_{10}-CO-Z \qquad (III)$$

in which: $R_{10}$ is chosen from divalent groups derived from a saturated dicarboxylic acid, mono- or dicarboxylic aliphatic acids comprising an ethylenic double bond, esters of lower alkanols, comprising from 1 to 6 carbon atoms, of these acids, and groups derived from the addition of any one of said acids to a bis(primary) or bis(secondary) amine, and Z is a group derived from a bis(primary), mono- or bis (secondary) polyalkylene-polyamine and, in at least one embodiment, may represent:

a) in an amount ranging from 60 to 100 mol %, the group

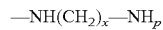

$$-NH(CH_2)_x-NH_p$$

where x=2 and p=2 or 3, or alternatively, x=3 and p=2 this group being derived from diethylenetriamine, from triethylenetetraamine, or from dipropylenetriamine;

b) in an amount ranging from 0 to 40 mol %, the group (IV) above in which x=2 and p=1 and which is derived from ethylenediamine, or the group derived from piperazine:

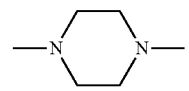

c) in an amount ranging from 0 to 20 mol %, the $-NH-(CH_2)_6-NH-$ group derived from hexamethylenediamine, these polyamino amides being crosslinked by addition reaction of a difunctional crosslinking agent chosen from epihalohydrins, diepoxides, dianhydrides, and bis-unsaturated derivatives, using from 0.025 to 0.35 mol of crosslinking agent per amine group of the polyamino amide and acylated by the action of an entity chosen from acrylic acid, chloroacetic acid, an alkane sultone, and salts thereof.

The saturated carboxylic acids may be chosen from acids comprising from 6 to 10 carbon atoms, such as adipic acid, 2,2,4-trimethyladipic acid, 2,4,4-trimethyladipic acid, terephthalic acid, and acids comprising an ethylenic double bond, for instance acrylic acid, methacrylic acid, and itaconic acid.

The alkane sultones used in the acylation may be chosen, for example, from propane sultone and butane sultone, and the salts of the acylating agents may be chosen from sodium and potassium salts.

(4) polymers comprising zwitterionic units of the following formula:

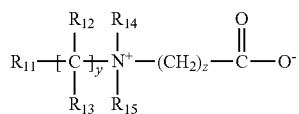

in which: $R_1$ is a polymerizable unsaturated group, for example, an acrylate, methacrylate, acrylamide, and methacrylamide group, y and z, which may be identical or different, are integers ranging from 1 to 3, $R_{12}$ and $R_{13}$, which may be identical or different, are chosen from hydrogen and methyl, ethyl, and propyl groups, and $R_{14}$ and $R_{15}$, which may be identical or different, are chosen from hydrogen and alkyl groups such that the sum of the carbon atoms in Ry and Ry does not exceed 10.

The polymers comprising such units may also contain units derived from nonzwitterionic monomers such as dimethylaminoethyl acrylate, dimethylaminoethyl methacrylate, diethylaminoethyl acrylate, diethylaminoethyl methacrylate, alkyl acrylates, alkyl methacrylates, acrylamides, methacrylamides, and vinyl acetate. Non-limiting example of such copolymers include butyl methacrylate/N,N-dimethylcarboxyaminoethyl methacrylate copolymers.

(5) polymers derived from chitosan comprising monomer units chosen from units of formula (D)-(F):

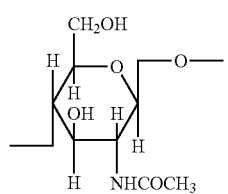

(D)

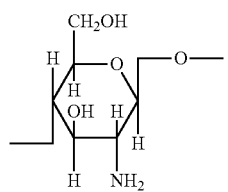

(E)

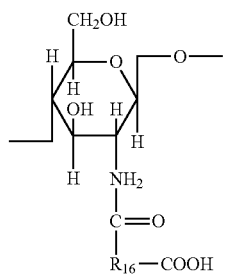

(F)

the unit (D) being present in an amount ranging from 0% to 30%, the unit (E) in an amount ranging from 5% to 50%, and the unit (F) in an amount ranging from 30% to 90%, it being understood that, in this unit (F), $R_{16}$ is a group of formula:

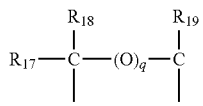

in which, if q=0, $R_{17}$, $R_{18}$, and $R_{19}$, which may be identical or different, are chosen from hydrogen, methyl, hydroxyl, acetoxy, and amino residues, monoalkylamine residues and dialkylamine residues that are optionally interrupted by at least one nitrogen atom and/or optionally substituted with at least one group chosen from amine, hydroxyl, carboxyl, alkylthio, and sulfonic groups, alkylthio residues in which the alkyl group comprises an amino residue, at least one of the groups $R_{17}$, $R_{18}$, and $R_{19}$ being, in this case, a hydrogen atom; or, if q=1, $R_{17}$, $R_{18}$, and $R_{19}$ are each hydrogen atoms, as well as the acid and base addition salts of these compounds.

(6) polymers described, for example, in French Patent No. 1 400 366 and comprising the repeating unit of the following formula:

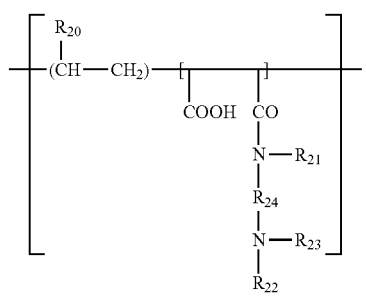

in which: $R_{20}$ is chosen from hydrogen, $CH_3O$, $CH_3CH_2O$, and phenyl groups, $R_{21}$ is chosen from hydrogen and lower alkyl groups such as methyl and ethyl, $R_{22}$ is chosen from hydrogen and $C_1$-$C_6$ lower alkyl groups such as methyl and ethyl, $R_{24}$ is chosen from —$CH_2$—$CH_2$—, —$CH_2$—$CH_2$—$CH_2$—, and —$CH_2$—$CH(CH_3)$— groups, and $R_{23}$ is chosen from C1-C6 lower alkyl groups such as methyl and ethyl and groups corresponding to the formula: —$R_{24}$—$N(R_{22})_2$—, wherein $R_{24}$ is chosen from —$CH_2$—$CH_2$—, —$CH_2$—$CH_2$—$CH_2$—, and —$CH_2$—$CH(CH_3)$— groups, and $R_{22}$ has the definition given above.

(7) polymers derived from the N-carboxyalkylation of chitosan, such as N-carboxymethylchitosan and N-carboxybutylchitosan.

(8) amphoteric polymers of the type -D-X-D-X chosen from:

a) polymers obtained by the action of chloroacetic acid or sodium chloroacetate on compounds containing at least one unit of formula:

-D-X-D-X-D- wherein D denotes a group

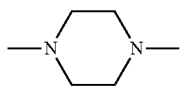

and X is chosen from the symbols E or E', wherein E or E', which may be identical or different, are chosen from divalent groups that are alkylene groups comprising a straight or branched chain comprising up to 7 carbon atoms in the main chain, which is unsubstituted or substituted with hydroxyl groups and which may contain, in addition to oxygen, nitrogen, and sulfur atoms, 1 to 3 aromatic and/or heterocyclic rings; the oxygen, nitrogen, and sulfur atoms being present in the form of an entity chosen from ether, thioether, sulfoxide, sulfone, sulfonium, alkylamine, and alkenylamine groups, hydroxyl, benzylamine, amine oxide, quaternary ammonium, amide, imide, alcohol, ester, and/or urethane groups.

b) polymers of formula:

-D-X-D-X- wherein D denotes a group

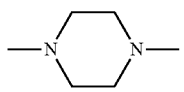

and X is chosen from the symbols E and E', and at least once E'; E having the meaning given above and E' being a divalent group that is an alkylene group with a straight or branched chain having up to 7 carbon atoms in the main chain, which is unsubstituted or substituted with at least one hydroxyl group and containing at least one nitrogen atom, the nitrogen atom being substituted with an alkyl chain that is optionally interrupted by an oxygen atom and comprising at least one carboxyl function or at least one hydroxyl function and betainized by reaction with an entity chosen from chloroacetic acid and sodium chloroacetate.

(9) (C1-C5) alkyl vinyl ether/maleic acid copolymers partially modified by semiamidation with an N,N-dialkylaminoalkylamine such as N,N-dimethylaminopropylamine or by semiesterification with an N,N-dialkylaminoalkynol. These copolymers may also contain other vinyl comonomers such as vinylcaprolactam.

The polyacid of the present disclosure may also be chosen from silicone acids such as polysilicone-8 (3M brand silicones "Plus" polymer VS 80, commercially available from 3M company) which has the structure:

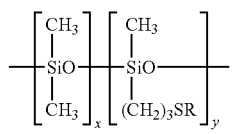

where R represents the acrylates copolymer radical.

In some instances, the polymeric acid and polymeric acid anhydride compound is chosen from VA/crotonates copolymer (and) isopropyl alcohol, Butyl ester of PVM/MA copolymer, isopropyl ester of PVM/MA copolymer, Ethyl ester of PVM/MA copolymer, VA/crotonates/vinyl neodecanoate copolymer, VA/crotonates copolymer, Ethylene/acrylic acid copolymer, VA/vinyl butyl benzoate/crotonates copolymer, Acrylates/octylacrylamide copolymer, Acrylates/t-Butylacrylamide copolymer, VP/acrylates/lauryl methacrylate copolymer, Styrene/acrylates copolymer, Acrylates copolymer, Polyacrylate-3, Carbomer, Acrylates/C10-30 alkyl acrylate crosspolymer and mixtures thereof.

In some cases, the polymeric acid and polymeric acid anhydride compound is one more maleic acid and/or maleic anhydride polymers. The one or more maleic acid and/or maleic anhydride polymers may be homopolymers and/or copolymers. Non-limiting examples of maleic anhydride copolymers include poly(styrene-alt-maleic anhydride), poly(methyl vinyl ether-alt-maleic anhydride), poly(ethylene-g-maleic anhydride), poly(isobutylene-alt-maleic anhydride), polyisoprene-g-maleic anhydride, poly(maleic anhydride-alt-1-octadecene), poly(ethylene-co-ethyl acrylate-co-maleic anhydride), polyethylene-graft-maleic anhydride, and mixtures thereof.

Non-limiting examples maleic acid copolymers selected from the group consisting of butyl ester of ethylene/MA copolymer, butyl ester of PVM/MA copolymer, calcium/sodium salt of PVM/MA copolymer, ethyl ester of PVM/MA copolymer, ethylene/MA copolymer, isobutylene/MA copolymer, isopropyl ester of PVM/MA copolymer, octadecene/MA copolymer, polyethylene/isopropyl maleate/MA copolymer, polyvinyl methyl ether (PVM)/MA copolymer, PVM/MA decadiene crosspolymer, sodium C4-C12 olein/maleic acid copolymer, sodium isooctylene/MA copolymer, sodium MA/diisobutylene copolymer, sodium PVM/MA/decadiene crosspolymer, stearylvinyl ether/MA copolymer, styrene/MA copolymer, and mixtures thereof.

The maleic acid polymer may include homopolymers and copolymers of maleic acid. In one embodiment, the maleic acid polymer has a molecular weight of between about 500 and about 5,000 g/mol. Examples of suitable maleic acid polymers include AQUATREAT AR-801 available from Alco Chemical, Chattanooga, Tenn., OPTIDOSE 4210 available from Dow and BELCLENE 200 available from Houghton Chemical Corporation.

In some cases, the maleic acid polymer is a maleic/methylvinyl ether copolymer (PVM/MA copolymer), which may have a molecular weight of between about 125,000 g/mol and about 800,000 g/mol, and/or a polydispersity index of between about 2 and 6. The maleic and methylvinyl ether monomer segments may be randomly arranged and/or have alternating segments such that the resulting maleic/methylvinyl ether copolymer has the following general structure:

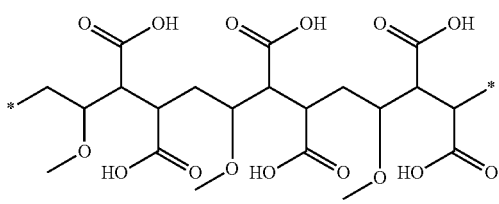 [SMILES: *CC(OC)C(C(=O)O)C(CC(OC)C(C(=O)O)C(CC(OC)C(C(=O)O)C(*)C(=O)O)C(=O)O)C(=O)O]

Examples of suitable maleic/methylvinyl ether copolymers are commercially available from ISP under the tradename "GANTREZ," as well as other suppliers such as SigmaAldrich. Mixtures of maleic acid polymers and maleic/methylvinyl ether copolymers may also be employed.

The polymeric acid and polymeric acid anhydride compound, in some cases, can be a poly(maleic anhydride/alkene-1) compound. The "maleic anhydride" component in this case includes α,β,-olefinically unsaturated dicarboxylic acid anhydride comonomers represented by the structural formula:

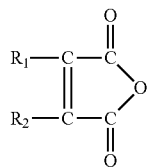

wherein $R_1$ and $R_2$ are independently selected from the group consisting of hydrogen, halogen, cyano, and aliphatic and aromatic substituents such as alkyl, aryl, alkaryl, aralkyl, cycloaliphatic, and the like, containing between one and about ten carbon atoms.

Compounds corresponding to the above formula include maleic anhydride, chloromaleic anhydride, 2,3-dichloromaleic anhydride, cyanomaleic anhydride, 2,3-dicyanomaleic anhydride, methylmaleic anhydride, 2,3-dimethylmaleic anhydride, ethylmaleic anhydride, propylmaleic anhydride, butylmaleic anhydride, 2,3-di-n-butylmaleic anhydride, phenylmaleic anhydride, benzylmaleic anhydride, cyclohexylmaleic anhydride, and the like.

The term "alkene-1" is meant to include alphaolefinically unsaturated hydrocarbons containing between 2 and about 6 carbon atoms. Illustrative of preferred alkene-1 comonomers are ethylene, Propylene, isobutylene, butene-1, pentene-1 and hexene-1.

Other maleic anhydride polymers include, but are not limited to, A-C 573 A (ETHYLENE-MALEIC ANHYDRIDE COPOLYMER) from Honeywell, A-C 596 A (PROPYLENE-MALEIC ANHYDRIDE COPOLYMER) from Honeywell, A-C 597 (PROPYLENE-MALEIC ANHYDRIDE COPOLYMER) from Honeywell, ZEMAC copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly (ethylene-co-butyl acrylate-co-maleic anhydride) sold under the trade name of LOTADER (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the LOTADER name, and isobutylene maleic anhydride copolymer sold under the name ACO-5013 by ISP.

The total amount of the one or more polymeric acid and polymeric acid anhydride compounds will vary depending on the composition. The total amount of the one or more polymeric acid and polymeric acid anhydride compounds may be about 0.01 to about 10 wt. %, about 0.01 to about 5 wt. %, about 0.01 to about 4 wt. %, about 0.01 to about 3 wt. %, about 0.01 to about 2 wt. %, about 0.1 to about 10 wt. %, about 0.1 to about 5 wt. %, about 0.1 to about 4 wt. %, about 0.1 to about 3 wt. %, or about 0.1 to about 2 wt. %, based on the total weight of the composition.

Active Agents

Oxidizing Agents

Oxidizing agents may be selected from, for example, peroxides, persulfates, perborates percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof.

One or more oxidizing agents are typically included in an oxidizing composition. An oxidizing composition may be a hair lightening or bleaching composition or it may be a neutralizing composition or a developer composition. In some cases, the total amount of the one or more oxidizing agents in an oxidizing composition is essentially 100% (as is the case for some powdered oxidation compositions). In some cases, the total amount of the one or more oxidizing agents is about 1 to about 80 wt. %, about 1 to about 70 wt. %, about 1 to about 60 wt. %, about 1 to about 50 wt. %, about 1 to about 40 wt. %, about 5 to about 80 wt. %, about 5 to about 70 wt. %, about 5 to about 60 wt. %, about 5 to about 50 wt. %, about 5 to about 40 wt. %, about 10 to about 80 wt. %, about 10 to about 70 wt. %, about 10 to about 60 wt. %, about 10 to about 50 wt. %, or about 10 to about 40 wt. %, based on the total weight of the composition.

Reducing Agents

Reducing agents are well known for use in hair care compositions. Typical reducing agents are capable of reducing the disulfide bonds in the hair to produce free thiol groups. Non-limiting examples of suitable reducing agents includethioglycolic acid and thioglycolic acid salts and esters, thiolactic acid and thiolactic acid salts and esters, cysteine thioglycerol, thioglycolic hydrazide, thioglycolamide, glycerol monothioglycolate, sodium metabisulfite, beta-mercaptopropionic acid, N-hydroxyethyl mercapto-acetamide, N-methyl mercapto-acetamide, beta-mercapto-ethylamine, beta-mercaptopropionamide, 2-mercapto-ethanesulfonic acid, dimercaptoadipic acid, dithiothreitol, homocysteinethiolactone, cysteine derivatives, polythiol derivatives formed by the addition of cysteamine onto a maleic anhydride-alkylvinylether copolymer, inorganic sulfites, inorganic bisulfites, cysteamine and its derivatives, dithioerythritol, organic phosphines, and mixtures thereof.

One or more reducing agents may be included in reducing compositions. The total amount of the one or more reducing agents can vary, but in some cases, the total amount of the one or more reducing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Non-Reducing Agents for Shaping Hair

Non-reducing agents for shaping hair may be one or more hydroxide compounds, non-hydroxide compounds, or mixtures thereof. For instance, the hydroxide compounds may be alkali metal hydroxides, alkaline-earth metal hydroxides, transition metal hydroxides, and mixtures thereof. Non-limiting examples include of hydroxide compounds include sodium hydroxide, potassium hydroxide, lithium hydroxide, calcium hydroxide, magnesium hydroxide, barium hydroxide, strontium hydroxide, manganese hydroxide, zinc hydroxide, guanidine hydroxide, and mixtures thereof.

Neutralizing Agents

Neutralizing agents are well known for use in hair care compositions. In some cases, after treating hair with compositions of the present disclosure comprising active agents chosen from reducing agents for curling or shaping the hair (as in perming and hair straightening systems), the hair is treated with a neutralizing agent or composition containing a neutralizing agent. For instance, the neutralizing agent may be an oxidizing agent chosen from hydrogen peroxide, urea hydrogen peroxide, alkali metal bromates, or persalts, such as perborates and persulphates. One or more neutralizing agents may be included in neutralizing compositions. The total amount of the one or more neutralizing agents can vary, but in some cases, the total amount of the one or more neutralizing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Colorants

Before, after, or simultaneously with the hair lightening composition, a color-altering composition may be used. For example, the color-altering composition may be formed by combining a hair lightening composition according to the instant disclosure, a developer composition (typically comprising hydrogen peroxide) and a colorant. Typically, the coloring compositions of the present disclosure include at least one colorant compound chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta.-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropano-I, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5- a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-β-hydroxyethylamino-3,4-methylene-dioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

| | |
|---|---|
| Het$^+$—C(R$^a$)=N—N(R$^b$)—Ar, An$^-$ | (Va) |
| Het$^+$—N(Ra)—N=C(Rb)—Ar, An$^-$ | (V'a) |
| Het$^+$—N=N—Ar, An$^-$ | (VIa) |
| Ar$^+$—N=N—Ar'', An$^-$ | (VI'a) and |
| Het$^+$—N=N—Ar'-N=N—Ar, An$^-$ | (VIIa) | in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more $(C_1-C_8)$ alkyl groups such as methyl;

Ar$^+$ representing an aryl radical, such as phenyl or naphthyl, bearing an exocyclic cationic charge, preferentially ammonium, particularly tri$(C_1-C_8)$alkylammonium such as trimethylammonium;

Ar represents an aryl group, especially phenyl, which is optionally substituted, preferentially with one or more electron-donating groups such as i) optionally substituted $(C_1-C_8)$alkyl, ii) optionally substituted $(C_1-C_8)$alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$alkoxy Ar'' is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

R$^a$ and R$^b$, which may be identical or different, represent a hydrogen atom or a group $(C_1-C_8)$alkyl, which is optionally substituted, preferentially with a hydroxyl group;

or alternatively the substituent R$^a$ with a substituent of Het$^+$ and/or R$_b$ with a substituent of Ar and/or R$^a$ with R$_b$ form, together with the atoms that bear them, a (hetero)cycloalkyl;

particularly, R$^a$ and R$_b$ represent a hydrogen atom or a group $(C_1-C_4)$alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

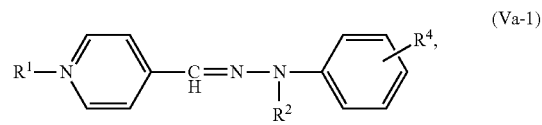

(Va-1)

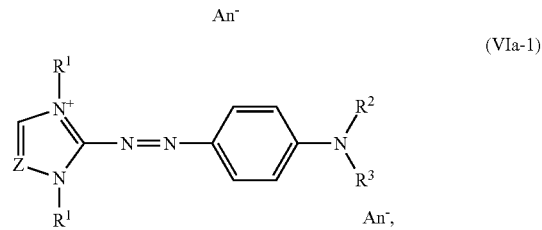

(VIa-1)

wherein in formulae (Va-1) and (VIa-1):

R$^1$ representing a $(C_1-C_4)$ alkyl group such as methyl;

R$^2$ and R$^3$, which are identical or different, represent a hydrogen atom or a $(C_1-C_4)$alkyl group, such as methyl; and R$^4$ represents a hydrogen atom or an electron-donating group such as optionally substituted $(C_1-C_8)$alkyl, optionally substituted $(C_1-C_8)$alkoxy, or (di)$(C_1-C_8)$(alkyl)amino optionally substituted on the alkyl group(s) with a hydroxyl group; particularly, R$^4$ is a hydrogen atom, Z represents a CH group or a nitrogen atom, preferentially CH;

An$^-$ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

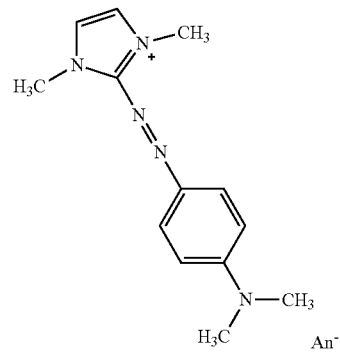

Basic Red 51

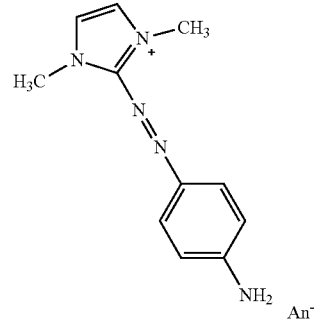

Basic Orange 31

Basic Yellow 87

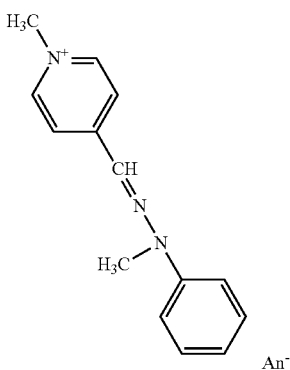

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Mono-Di-, and Tri-Carboxylic Acids

The mono-, di-, and/or tri-carboxylic acids may be chosen especially from linear, branched and/or cyclic, saturated or unsaturated, or even aromatic, polycarboxylic acids, containing 2 to 50 or 2 to 40 carbon atoms, in particular 3 to 36, 3 to 18, or 4 to 12 carbon atoms, or even 5 to 10 carbon atoms; the acid comprising one, two, or three carboxylic groups COOH; and possibly comprising 1 to 10 or 1 to 6 identical or different heteroatoms, chosen from O, N and S; and/or possibly comprising at least one perfluoro radical chosen from —CF$_2$— (divalent) or —CF$_3$.

In some cases, the mono-, di-, and/or tri-carboxylic acids are saturated, linear and aliphatic and contain 2 to 36 carbon atoms or 3 to 18 carbon atoms or even 4 to 12 carbon atoms; or alternatively are aromatic and contain 8 to 12 carbon atoms.

The cyclic anhydride of a polycarboxylic acid may correspond to one of the following formulae:

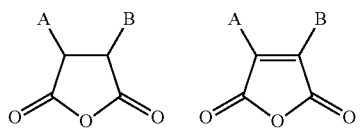

in which the groups A and B are, independently of each other: a hydrogen atom, a saturated or unsaturated, linear, branched and/or cyclic aliphatic, or alternatively aromatic, carbon-based radical; containing 1 to 16 carbon atoms, 2 to 10 carbon atoms or even 4 to 8 carbon atoms, especially methyl or ethyl, or alternatively A and B taken together form a saturated or unsaturated, or even aromatic, ring comprising in total 5 to 14, especially 5 to 10 or even 6 to 7 carbon atoms. In some cases, A and B represent a hydrogen atom or together form an aromatic ring containing in total 6 to 10 carbon atoms.

Among the mono-, di-, and/or tri-carboxylic acids or anhydrides thereof that may be used, mention may be made, alone or as a mixture, of: dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid and fatty acid dimers (especially of C$_{36}$); tricarboxylic acids such as cyclohexanetricarboxylic acid, trimellitic acid, 1,2,3-benzenetricarboxylic acid and 1,3,5-benzenetricarboxylic acid, tetracarboxylic acids such as butanetetracarboxylic acid and pyromellitic acid, cyclic anhydrides of these acids and especially phthalic anhydride, trimellitic anhydride, maleic anhydride and succinic anhydride.

Mention may also be made of mono-, di-, and/or tri-carboxylic acids chosen, alone or as a mixture, from:

(i) mono-, di-, and/or tri-carboxylic acids containing a saturated or unsaturated, linear or branched chain comprising at least one heteroatom chosen from O, N and/or S, especially 1 to 10 identical or different heteroatoms, and/or comprising at least one perfluoro radical —CF$_2$— or —CF$_3$ and moreover containing 1, 2, or 3 carboxylic groups COOH; and/or a cyclic anhydride of such a polycarboxylic acid; and/or (ii) saturated or unsaturated, or even aromatic, heterocyclic mono-, di-, and/or tri-carboxylic acids comprising at least one heteroatom chosen from O, N and/or S, especially 1 to 10, or even 1 to 4, identical or different heteroatoms, and 1, 2, or 3 carboxylic groups COOH; and/or a cyclic anhydride of such a polycarboxylic acid; and/or (iii) sugar-based mono-, di-, and/or tri-carboxylic acids, which may be obtained especially by oxidation of an aldose, and comprising 1, 2, or 3 carboxylic groups COOH; and/or a cyclic anhydride of such a polycarboxylic acid; and/or (iv) itaconic anhydride;

(v) mono-, di-, and/or tri-carboxylic acids (including heterocyclic) amino acids, i.e. polycarboxylic acids containing a saturated or unsaturated, linear, branched and/or cyclic chain, optionally comprising at least one heteroatom chosen from O, N and/or S, especially 1 to 10 identical or different heteroatoms, and/or optionally comprising at least one perfluoro radical —CF$_2$— or —CF$_3$; and also comprising at least one primary, secondary or tertiary amine function (especially NR$^1$R$^2$ with R$^1$ and R$^2$, independently of each other, chosen from H and C$_1$-C$_{12}$ alkyl), especially 1 to 3 identical or different amine functions, and moreover containing 1, 2, or 3 carboxylic acid groups COOH; and/or a cyclic anhydride of such a polycarboxylic acid.

Mention may be made most particularly, alone or as a mixture, of the following di-carboxylic acids: (i) 2,2'-[1,5-pentanediylbis(thio)]bis-acetic acid 6,6'-[(1,2-dioxo-1,2-ethanediyl)diimino]bis-hexanoic acid 2,2'-sulfinylbis-acetic acid 4,13-dioxo-3,5,12,14-tetraazahexadecanedioic acid poly(ethylene glycol)disuccinate, especially of mass 250-600 poly(ethylene glycol)bis(carboxymethyl) ether, especially of mass 250-600 poly[oxy(1,2-dicarboxy-1,2-ethanediyl)], especially of DP<10 8-[(carboxymethyl)amino]-8-oxooctanoic acid 2,2'-[methylenebis(sulfonyl)]bis-acetic acid 4,4'-(1,6-hexanediyldiimino)bis[4-oxobutanoic acid] 4,9-dioxo-3,5,8,10-tetraazadodecanedioic acid 4-[(1-carboxyethyl)amino]-4-oxobutanoic acid 6-[(3-carboxy-1-oxopropyl)amino]hexanoic acid N,N'-(1,6-dioxo-1,6- hexanediyl)bis-glycine N,N'-(1,6-dioxo-1,6-hexanediyl)bisphenylalanine N,N'-(1,3-dioxo-1,3-propanediyl)bis-glycine 4,4'-[(1,4-dioxo-1,4-butanediyl)diimino]bis-butanoic acid 4,4'-[(1,6-hexanediyl)diimino]bis-butanoic acid 6,6'-[1,6-hexanediylbis(iminocarbonylimino)]bis-hexanoic acid N-benzoyl-S-(carboxymethyl)cysteine N,N'(2,2,3,3-tetrafluoro-1,4-dioxo-1,4-butanediyl)bis-glycine N,N'-(2,2,3,3-tetrafluoro-1,4-dioxo-1,4-butanediyl)bis-alanine 4,4'-[(2,2,3,3-tetrafluoro-1,4-dioxo-1,4-butanoic acid N,N'(1,5-dioxo-1,5-pentanediyl)bis-glycine N,N'-(1,9-dioxo-1,9-nonanediyl)bis-glycine N,N'-(1,10-dioxo-1,10-decanediyl)bis[N-methyl]glycine bis(3-carboxypropyl)ester of propanedioic acid 7,16-dioxo-6,8,15,17-tetraazadocosanedioic acid N-benzoyl-N-(2-carboxyethyl)glycine [2-[(2-carboxymethyl)amino]-2-oxoethyl]benzenepropanoic acid [2-[(2-carboxyethyl)amino]-2-oxoethyl]benzenepropanoic acid (ii) 4,7,9,12-tetraoxapentadecanedioic acid 2,3-pyridinedicarboxylic acid 4-pyranone-2,6-dicarboxylic acid 2,5-pyrazinedicarboxylic acid 2,5-pyridinedicarboxylic acid 2,3-benzofurandicarboxylic acid 7-oxabicyclo[2.2.1]heptane-2,3-dicarboxylic acid 3,4-pyridinedicarboxylic acid 2,4-pyridinedicarboxylic acid 3,5-pyridinedicarboxylic acid 2,6-pyridinedicarboxylic acid 1H-imidazole-4,5-dicarboxylic acid 2,3-quinolinedicarboxylic acid 6,6,7,7-tetrafluoro-3-oxabicyclo[3.2.0]heptane-2,4-dicarboxylic acid 2,6-pyrazinedicarboxylic acid 2,6-dimethyl-3,5-pyridinedicarboxylic acid 1-phenyl-1H-pyrazole-3,4-dicarboxylic acid 2,5-furandicarboxylic acid 3,4-furandicarboxylic acid 1,2,5-thiadiazole-3,4-dicarboxylic acid 1,4-dihydro-1,2,4,5-tetrazine-3,6-dicarboxylic acid 2,3-furandicarboxylic acid 3,4-thiophenedicarboxylic acid 1H-1,2,3-triazole-4,5-dicarboxylic acid 2-methylimidazole-4,5-dicarboxylic acid 2,4-quinolinedicarboxylic acid naphtho[2,1-b]furan-1,2-dicarboxylic acid 3,4-quinolinedicarboxylic acid 7-oxabicyclo[2.2.1]hept-5-ene-2,3-dicarboxylic acid 2,3-quinoxalinedicarboxylic acid 1,4-piperazinedicarboxylic acid 2,5-dimethyl-3,4-furandicarboxylic acid tetrahydro-2,5-thiophenedicarboxylic acid 4-phenyl-3,5-pyridinedicarboxylic acid thieno[3,2-b]thiophene-2,5-dicarboxylic acid 3-methyl-2,4-thiophenedicarboxylic acid naphthostyril-5,6-dicarboxylic acid 3-phenyl-2,4-quinolinedicarboxylic acid 3,4-dimethyl-2,5-dicarboxythiophene 3,4-diphenyl-2,5-thiophenedicarboxylic acid 2,5-diphenyl-3,4-furandicarboxylic acid 7-oxo-7H-benzimidazo[2,1-a]benz[de]isoquinoline-3,4-dicarboxylic acid 2,3-dihydro-1,3-dioxo-1H-benz[de]isoquinoline-6,7-dicarboxylic acid 3,4-bis(phenylmethoxy)-2,5-furandicarboxylic acid 4,4'-bibenzoic acid-2,2'-sulfone 2,7-diphenyl-m-anthrazoline-4,5-dicarboxylic acid 2,4-pyrimidinedicarboxylic acid 2-phenyl-4,5-thiazoledicarboxylic acid 6-phenyl-2,3-pyridinedicarboxylic acid 5,6-dimethyl-2,3-pyrazinedicarboxylic acid 3,7-dibenzothiophenedicarboxylic acid 9-oxo-9H-xanthene-1,7-dicarboxylic acid 2-(1,1-dimethylethyl)-H-imidazole-4,5-dicarboxylic acid 6,7-quinolinedicarboxylic acid 6-methyl-2,3-pyridinedicarboxylic acid 4,5-pyrimidinedicarboxylic acid 2-methyl-3,4-furandicarboxylic acid 1,2-indolizinedicarboxylic acid 2,8-dibenzothiophenedicarboxylic acid 3,6-pyridazinedicarboxylic acid 1,10-phenanthroline-2,9-dicarboxylic acid 1,4,5,6-tetrahydro-5,6-dioxo-2,3-pyrazinedicarboxylic acid 3,4-dimethoxy-2,5-furandicarboxylic acid 2-ethyl-4,5-imidazoledicarboxylic acid 2-propyl-1H-imidazole-4,5-dicarboxylic acid 4-phenyl-2,5-pyridinedicarboxylic acid 4,5-pyridazinedicarboxylic acid 1,4,5,8-tetrahydro-1,4:5,8-diepoxynaphthalene-4a,8a-dicarboxylic acid 5,5-dioxide-2,8-dibenzothiophenedicarboxylic acid pyrazolo[1,5-a]pyridine-2,3-dicarboxylic acid 2,3-dihydro-1H-pyrrolizine-1,7-dicarboxylic acid 6-methyl-2,4,5-pyridinetricarboxylic acid pyrrolo[2,1,5-cd]indolizine-5,6-dicarboxylic acid 3,4-bis(2,2,3,3,4,4,4-heptafluorobutyl)-1H-pyrrole-2,5-dicarboxylic acid 6,7,9,10,17,18,20,21-octahydrodibenzo[b,k]-[1,4,7,10,13,16]hexaoxacyclooc-tadecin-2,14-dicarboxylic acid 6,7,9,10,17,18,20,21-octahydrodibenzo[b,k]-[1,4,7,10,13,16]hexaoxacyclooc-tadecin-2,13-dicarboxylic acid 2-methyl-3,4-quinolinedicarboxylic acid 4,7-quinolinedicarboxylic acid 3,5-isoxazoledicarboxylic acid 2-(trifluoromethyl)-3,4-furandicarboxylic acid 5-(trifluoromethyl)-2,4-furandicarboxylic acid 6-methyl-2,4-quinolinedicarboxylic acid 5-oxo-1,2-pyrrolidinedicarboxylic acid 5-ethyl-2,3-pyridinedicarboxylic acid 1,2-dihydro-2-oxo-3,4-quinolinedicarboxylic acid 4,6-phenoxathiindicarboxylic acid 10,10-dioxide 1,9-phenoxathiindicarboxylic acid 3,4-dihydro-2H-1,4-thiazine-3,5-dicarboxylic acid 2,7-di(tert-butyl)-9,9-dimethyl-4,5-xanthenedicarboxylic acid 6-methyl-2,3-quinoxalinedicarboxylic acid 3,7-quinolinedicarboxylic acid 2,5-quinolinedicarboxylic acid 2-methyl-6-phenyl-3,4-pyridinedicarboxylic acid 3,4-dimethylthieno[2,3-b]thiophene-2,5-dicarboxylic acid 3,4-dimethoxythiophene-2,5-dicarboxylic acid 5-methyl-3,4-isoxazoledicarboxylic acid 2,6-bis(aminocarbonyl)-3,5-pyridinedicarboxylic acid 3,5-bis(aminocarbonyl)-2,6-pyrazinedicarboxylic acid 2,3-pyridinedicarboxylic acid 6-(1,1-dimethylethyl)-2-ethyl-3,4-pyridinedicarboxylic acid 3-methyl-5-phenyl-2,4-thiophenedicarboxylic acid 1,2-dihydro-2-oxo-6-phenyl-3,5-pyridinedicarboxylic acid 8-methyl-2,4-quinolinedicarboxylic acid 4-ethyl-2,6-dimethyl-3,5-pyridinedicarboxylic acid 5-(phenoxymethyl)-2,4-furandicarboxylic acid 5-(acetylamino)-3-methyl-2,4-thiophenedicarboxylic acid 2-(4-heptylphenyl)-4,8-quinolinedicarboxylic acid 2,8-bis(4-heptylphenyl)pyrido[3,2-g]quinoline-4,6-dicarboxylic acid 1,2,3,4,6,7,8,9-octahydro-2,8-dioxopyrido[3,2]-quinoline-3,7-dicarboxylic acid 2,8-dimethylpyrido[3,2-g]quinoline-3,7-dicarboxylic acid 5,6-quinolinedicarboxylic acid 6-ethyl-2-methylcinchomeronic acid 2-methyl-6-propylcinchomeronic acid 6-isopropyl-2-methylcinchomeronic acid 6-tert-butyl-2-methylcinchomeronic acid 1,4-dimethyl-7-oxabicyclo[2.2.1]heptane-2,3-dicarboxylic acid 1,2-dihydro-2-oxo-3,8-quinolinedicarboxylic acid 1,2-dihydro-2-oxo-3,6-quinolinedicarboxylic acid 1,2-dihydro-2-oxo-3,7-quinolinedicarboxylic acid 3,7-dimethyl-2,8-diphenylpyrido[3,2-g]quinoline-4,6-dicarboxylic acid 8-methyl-2,3-quinolinedicarboxylic acid 3-[[(1,1-dimethylethyl)amino]sulfonyl]-2,5-thiophenedicarboxylic acid 4-(acetylamino)-2,3-thiophenedicarboxylic acid 2,5-pyridinedicarboxylic acid 2,6-pyridinedicarboxylic acid 2,4-thiophenedicarboxylic acid 2,5-thiophenedicarboxylic acid 1,4-pyran-2,6-dicarboxylic acid (iii) ribaric acid glucaric acid xylaric acid arabinaric acid mannaric acid idaric acid altraric acid L-glucaric acid L-arabinaric acid allaric acid galactaric acid meso-tartaric acid D-glucaric acid L-idaric acid hexaric acid 2,3-dihydroxybutanedioic acid D-tartaric acid D,L-tartaric acid D-glucaric acid tartaric acid tetrahydroxysuccinic acid 2-carboxy-2,3-dideoxy-D-manno-2-octulopyranosonic acid methyl-3-deoxy-D-arabino-2-heptulopyranosaric acid D-lyxo-2-heptulopyranosaric acid 2,6-anhydro-L-glycero-L-galactoheptaric acid (iv) 1,4,5,8-naphthalenetetracarboxylic acid 1,4-monoanhydride itaconic anhydride (v) 1,4-dihydro-4-oxo-2,6-pyridinedicarboxylic acid 2,6-piperidinedicarboxylic acid 1H-pyrrole-3,4-dicarboxylic acid 4-amino-2,6-dicarboxylic acid 1-methyl-1H-pyrazole-3,4-dicarboxylic acid 2,3-piperidinedicarboxylic acid 1-methyl-1H-imidazole-4,5-dicarboxylic acid 2,4-thiazolidinedicarboxylic acid 1-(phenylmethyl)-1H-imidazole-4,5-dicarboxylic acid 5-amino-6-oxo-2,3-piperidinedicarboxylic acid 5-amino-6-oxo-2,4-piperidinedicarboxylic acid 5-amino-6-oxo-2,3-piperidinedicarboxylic acid 5-amino-6-oxo[2S-(2α,4β,5α)]-2,4-piperidinedicarboxylic acid (2S,4R)-2,4-pyrrolidinedicarboxylic acid (2S-cis)-2,4-pyrrolidinedicarboxylic acid 2-amino-1H-imidazole-4,5-dicarboxylic acid 2,5-pyrrolidinedicarboxylic acid 4-amino-3,5-isothiazoledicarboxylic acid 1-methyl-1H-pyrazole-3,5-dicarboxylic acid 7-(diethylamino)-2-oxo-2H-1-benzopyran-3,4-dicarboxylic acid 3,4-diethyl-1H-pyrrole-2,5-dicarboxylic acid 1-phenyl-1H-pyrrole-3,4-dicarboxylic acid cis-2,3-piperazinedicarboxylic acid 2,3-piperazinedicarboxylic acid 2,5-piperazinedicarboxylic acid 2,6-piperazinedicarboxylic acid 2-amino-3,5-pyridinedicarboxylic acid 2-methylpyrrole-3,4-dicarboxylic acid 4-(methylamino)-2,6-pyridinedicarboxylic acid 2-amino-6-methyl-3,4-pyridinedicarboxylic acid 5-amino-2-methyl-3,4-pyridinedicarboxylic acid 2-amino-6-methyl-3,5-pyridinedicarboxylic acid 2,5-dimethylpyrrole-3,4-dicarboxylic acid 2,5-dimethylpyrrole-3,4-dicarboxylic acid 2-amino-6-hydroxy-3,5-pyridinedicarboxylic acid 2,4-pyrrolidinedicarboxylic acid 1H-indole-2,4-dicarboxylic acid 1H-indole-2,6-dicarboxylic acid 1H-indole-2,5-dicarboxylic acid 5-phenyl-2,4-pyrrolidinedicarboxylic acid 5-methyl-2,4-pyrrolidinedicarboxylic acid trans-2,4-azetidinedicarboxylic acid cis-2,4-azetidinedicarboxylic acid 3,5-piperidinedicarboxylic acid 2,3-pyrrolidinedicarboxylic acid 2,3-azetidinedicarboxylic acid 3,4-pyrrolidinedicarboxylic acid 2,3-dihydro-6H-1,4-dioxino[2,3-c]pyrrole-5,7-dicarboxylic acid 1H-imidazole-2,4-dicarboxylic acid 1-butyl-1H-pyrrole-2,3-dicarboxylic acid 3-amino-1-oxide-2,4-pyridinedicarboxylic acid 2,3-dihydro-5-phenyl-1H-pyrrolizine-6,7-dicarboxylic acid 3a,4,5,9b-tetrahydro-3H-cyclopenta[c]quinoline-4,6-dicarboxylic acid 3a,4,5,9b-tetrahydro-3H-cyclopenta[c]quinoline-4,8-dicarboxylic acid 2,3-dihydro-1H-imidazole-4,5-dicarboxylic acid 5-amino-6-methyllutidinic acid 1H-indole-3,7-dicarboxylic acid 3,3-dimethyl-2,6-piperidinedicarboxylic acid 1-butyl-2,5-pyrrolidinedicarboxylic acid 1H-indole-4,6-dicarboxylic acid 1-(phenylmethyl)-3,4-pyrrolidinedicarboxylic acid 3-(carboxymethyl)-1H-indole-2,6-dicarboxylic acid 3,4-bis(2,2,2-trifluoroethyl)-1H-pyrrole-2,5-dicarboxylic acid 9-hexyl-9H-carbazole-3,6-dicarboxylic acid 3-methyl-5-(1-piperazinylsulfonyl)-2,4-thiophenedicarboxylic acid 2,3,4,9-tetrahydro-1H-carbazole-5,7-dicarboxylic acid 2,3-dimethyl-1H-indole-4,6-dicarboxylic acid 7-amino-1,4-dihydro-4-oxo-3,6-quinolinedicarboxylic acid 5-amino-3-methyl-2,4-thiophenedicarboxylic acid (m-tolylimino)diacetic acid (o-tolylimino)diacetic acid D-cystathionine phenethyliminodiacetic acid 2-benzyl-2,2'-iminodiacetic acid L-α-glutamyl-L-alanyl-L-alanine N,N'-dibenzylethylenediaminediacetic acid N-L-γ-glutamyl-D-alanine glycyl-L-glutamylglycine N-(carboxymethyl)-N-(tetrahydro-1,1-dioxido-3-thienyl)glycine N-(2-carboxyethyl)-N-phenyl-beta-alanine N-(carboxymethyl)-N-octylglycine N-(tert-butoxycarbonyl)iminodiacetic acid N-(carboxymethyl)-L-alanine N-(6-aminohexyl)-N-(carboxymethyl)glycine N-(carboxymethyl)-N-tetradecylglycine N-(1-carboxyethyl)-D-alanine N-(carboxymethyl)-D-alanine decyliminodiacetic acid 3,3'-(dimethylhydrazono)bis-propanoic acid N-(carboxymethyl)-N-[2-(2,6-dioxo-4-morpholinyl)ethyl]glycine N-alpha-aspartylglycine N-beta-aspartylglycine N-L-alpha-aspartyl-beta-alanine 3,4-xylylamino-N,N-diacetic acid N-(1-carboxyethyl)alanine N-(carboxymethyl)alanine N,N'-methylenebis-glycine N-(aminomethyl)-N-(carboxymethyl)glycine N-(aminomethyl)-N-(carboxymethyl)glycine 2,2'-(methylhydrazono)bis-acetic acid N-(2-carboxyethyl)-N-(4-methylphenyl)-beta-alanine N-(2-carboxyethyl)-N-(3-methylphenyl)-beta-alanine 3-[(carboxymethyl)amino]alanine D-alpha-aspartyl-D-alanine N-(2-carboxyethyl)-N-(1-oxohexadecyl)-beta-alanine N-(2-carboxyethyl)-N-(1-oxodecyl)-beta-alanine N-(2-carboxyethyl)-N-(1-oxotetradecyl)-beta-alanine amino[(carboxymethyl)thio]acetic acid N,N'-1,6-hexanediylbis-beta-alanine N-(carboxymethyl)-N-phenyl-beta-alanine N-(1-carboxyethyl)-L-alanine L-glutamic acid L-aspartic acid.

The total amount of the mono-, di-, and/or tri-carboxylic acids can vary depending on the type of composition. The total amount of mono-, di-, and/or tri-carboxylic acids is typically about 1 to about 50 wt. %, based on the total weight of the composition. In some cases, the total amount of the one or more mono-, di-, and/or tri-carboxylic acids is about 1 to about 40 wt. %, about 1 to about 30 wt. %, about 1 to about 25 wt. %, about 1 to about 20 wt. %, about 5 to about 50 wt. %, about 5 to about 40 wt. %, about 5 to about 30 wt. %, about 5 to about 25 wt. %, or about 5 to about 20 wt. %.

Amines

Monamines

Many monoamines are suitable for use herein. Non-limiting examples of monoamines methylamine, ethylamine, isopropylamine and n-propylamine, or of a diamine selected from the group consisting of ethylenediamine, 1,2-propanediamine, 1,3-propanediamine, 1,2-butanediamine, 1,3-butanediamine and 1,4-butanediamine or of an alkanolamine selected from the group consisting of monoethanolamine, 2-aminopropan-1-ol and 1-aminopropan-2-ol, or of a specialty amine selected from the group consisting of 1,2,3-triaminopropane, 1,3-diaminopropan-2-ol, 1,2-diamino-propan-3-ol, 1-aminopropanediol, 2-aminopropanediol, glucosamine and isomaltine and/or piperazine, or of a piperazine derivative selected from the group consisting of 2-methylpiperazine, 2,6-dimethylpiperazine, 2,5-dimethylpiperazine, 2,5-bis(aminomethyl)piperazine, 2,6-bis(aminomethyl)piperazine, 2-aminomethyl-5-methylpiperazine and 2-aminomethyl-6-methylpiperazine The monoamine may be an alkyl monoamine of the present disclosure are amine compounds having one amino group. Non-limiting examples of alkyl monoamines include aliphatic amine compounds corresponding to the following formula and their salts:

$$RN(R')_2 \qquad (IA)$$

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

In some cases, alkyl monoamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Other non-limiting examples of alkyl monoamines include amidoamine compounds corresponding to the following formula and their salts:

RCONHR'N(R")$_2$ wherein: R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. In some cases, R" is H or a methyl group.

Examples of amidoamines include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

The monoamine may be an alkoxylated monoamine. The alkoxylated monoamines are chosen from amine compounds having an amino group and at least one degree of alkoxylation. The alkoxylation is provided by an alkylene oxide group which is often chosen from ethylene oxide and propylene oxide.

Non-limiting examples of suitable alkoxylated monoamines include compounds corresponding to the following formula:

RN[(R'CHCH$_2$O)$_x$H][(R'CHCH$_2$O)$_y$H]

wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 provided that the sum of x+y is >0; the groups R', which may be identical or different, represent hydrogen, or an alkyl group such as a methyl group. Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Non-limiting examples of alkoxylated monoamines include PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding the following formula:

RNR"[(R'CHCH$_2$O)$_x$H]

wherein R is a hydrocarbon radical containing at least 6 carbon atoms. R can be linear or branched, acyclic or cyclic, saturated or unsaturated, aliphatic or aromatic, substituted or unsubstituted; x represents a number of from 1 to 100; R' represents hydrogen, or an alkyl group such as in particular a methyl group; and R" is a hydrogen or a hydrocarbon radical. Typically, R is a linear or branched, acyclic alkyl or alkenyl group or an alkyl phenyl group; x is typically a number from 1 to 30. When R" is a hydrocarbon radical group, this group may be linear or branched, saturated or unsaturated, substituted or unsubstituted. The hydrocarbon radical represented by R" may also contain an alkoxylated moiety (as defined by [(R'CHCH$_2$O)$_y$H]), and/or heteroatoms such as nitrogen. When R" contains at least one alkoxylated moiety, the total number of alkoxylation in the formula may range from 1 to 120. Examples of alkoxylated monoamines include PEG-3 Tallow Aminopropylamine, PEG-10 Tallow Aminopropylamine, PEG-15 Tallow Aminopropylamine, and PEG-105 Behenyl Propylenediamine.

Additional non-limiting examples of alkoxylated monoamines include compounds corresponding to the following formula:

R(R'CHCH$_2$O)$_x$(R'CHCH$_2$O)$_y$NH$_y$ wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 with the proviso that the sum of x+y is >0; the groups R', which may be identical or different, represent hydrogen, or an alkyl group such as in particular a methyl group. Typically, R is a linear or branched, acyclic alkyl or alkenyl group or an alkyl phenyl group; x and y, independently of one another, are each typically a number from 0 to 30. Examples of alkoxylated monoamines include polyetheramines containing a monoamine group. These polyetheramines are commercially available from Hunstman under the tradename JEFFAMINE (M series such as M-600, M-1000, M-2005 and M-2070) and SURFONAMINE series (B-60, B-100, B-200, L-100, L-200, L-207, L-300).

In some cases, the monamines may be selected from the group consisting of 3-isopropoxypropylamine, 3-methoxypropylamine, tris(hydroxymethyl)aminomethane, 3-ethoxypropylamine, 3-(2-ethylhexyloxy)-propylamine, 2-(2-aminoethoxy)ethanol, 3-butoxypropylamine, and monoethanolamine, and mixtures thereof;

Diamines

Non-limiting examples of diamines that may be useful may be primary amines and secondary amines. The diamine can include both primary and secondary amine groups. Optional diamines may include at least one ethylene oxide group. For example, between 1 and 4 ethylene oxide groups can be present in the diamine. The diamine may optionally include propylene oxide groups. For example, between 1 and 4 propylene oxide groups can be present in the diamine. Non-limiting examples of diamines include 4,9-dioxadodecane-diamine; 4,7,10-trioxa-1,13-tridecanediamine; ethylenediamino; polyoxypropylene diamine; polyethylene glycol diamine; triethylene glycol diamine (2OE); n-(2-hydroxyethyl)-ethylenediamine; 1,3-diaminopropane; 1,7-diaminoheptane; 1,4-diaminobutane; 1,2-diaminopropane;

1,6-diaminohexane; 1,11-diamino-3,6,9-trioxaundecane; 1,5-diaminopentane; polyoxyethylene diamine; 2,2-dimethyl-1,3-propanediamine; 2,2-bis(aminoethoxy)propane; 4,7,10-trioxa-1,13-tridecanediamine; 1,3-diaminopentane; 4,7,10-trioxa-1,13; 1,5-diamino-2-methylpentane; (3s,4s)-(−)-3,4-hexanediamine dihydrochloride; 1,9-diaminononane, and mixtures thereof.

In some cases, diamines may be selected from the group consisting of 4,9-dioxadodecane-diamine, 4,7,10-trioxa-1,13-tridecanediamine, ethylenediamino, polyoxypropylene diamine, polyethylene glycol diamine, triethylene glycol diamine (2OE); n-(2-hydroxyethyl)-ethylenediamine; 1,3-diaminopropane, 1,7-diaminoheptane, 1,4-diaminobutane, 1,2-diaminopropane, 1,6-diaminohexane, 1,11-diamino-3,6,9-trioxaundecane, 1,5-diaminopentane, polyoxyethylene diamine, 2,2-dimethyl-1,3-propanediamine, 2,2-bis(aminoethoxy)propane, 4,7,10-trioxa-1,13-tridecanediamine, 1,3-diaminopentane, 4,7,10-trioxa-1,13; 1,5-diamino-2-methylpentane, (3s,4s)-(−)-3,4-hexanediamine dihydrochloride, 1,9-diaminononane, and mixtures thereof.

Polyamines

Polyamines have more than two amino groups. In some cases, the composition of the instant disclosure may include one or more polyamines, but in some cases, the compositions are free or essentially free of polyamines. The polyamine may be, for example, aminated polysaccharides comprising multiple amino groups, such as, for example, hydrolysates of aminated polysaccharides.

The polyamine may also be a polymer comprising multiple amino groups including homopolymers, copolymers, and terpolymers.

In some cases, polyamines are chosen from polyethyleneimines. Polyethyleneimines may optionally be substituted. Non-limiting examples of polyethyleneimines which may be used include LUPASOL products commercially available from BASF. Suitable examples of LUPASOL polyethyleneimines include LUPASOL PS, LUPASOL PL, LUPASOL PR8515, LUPASOL G20, LUPASOL G35 as well as LUPASOL SC Polythyleneimine Reaction Products (such as LUPASOL SC-61B, LUPASOL SC-62J, and LUPASOL SC-86X). Other non-limiting examples of polyethyleneimines which may be used in the composition according to the present invention are the EPOMIN products commercially available from Aceto. Suitable examples of EPOMIN polyethyleneimines include EPOMIN SP-006, EPOMIN SP-012, EPOMIN SP-018, and EPOMIN P-1000. Suitable polyamines s also be chosen from polyvinylamines. Examples thereof include LUPAMINES 9095, 9030, 9010, 5095, 1595 from BASF.

The polyamine compounds can also be substituted. An example of such a compound is PEG-15 Cocopolyamine from Cognis.

In some cases, the polyamine is chosen from proteins and protein derivatives. Non-limiting examples of suitable proteins and protein derivatives f include those listed at pages 1701 to 1703 of the C.T.F.A. International Cosmetic Ingredient Dictionary and Handbook, 8$^{th}$ edition, vol. 2, (2000), which is incorporated herein by reference in its entirety. In some cases, the at least one polyamine is chosen from wheat protein, soy protein, oat protein, collagen, and keratin protein.

The polyamine may be an alkoxylated polyamine. The alkoxylated polyamines may be chosen from amine compounds having at least two amino groups and at least one degree of alkoxylation. The alkoxylation is provided by an alkylene oxide group which may be chosen from ethylene oxide and propylene oxide. Non-limiting examples of suitable alkoxylated polyamines include compounds corresponding to the following formula:

wherein R represents a —CH2—, —CH$_2$CH$_2$—, —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted; x, y, and z independently of one another, represent numbers of from 0 to about 100; R' represents hydrogen, or an alkyl group, preferably a methyl group; and The sum of x+y+z is at least 1. In some cases, R is a linear or branched, acyclic alkyl or alkenyl group or an alkyl phenyl group; x, y, and z independently of one another, preferably represent numbers ranging from 2 to 100.

Non-limiting examples of the alkoxylated polyamines include, for example, tetradecyloxypropyl-1,3-diaminopropane; a C$_{12-14}$ alkyl oxypropyl-1,3-diaminopropane; a C$_{12-15}$ alkyloxypropyl amine and other similar materials that are commercially available from Tomah under the tradename of TOMAH DA-17. Other examples of alkoxylated polyamines are diamine compounds belonging to the Jeffamine series such as the JEFFAMINE D and JEFFAMINE ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. JEFFAMINE D series compounds are amine terminated PPGs (polypropylene glycols) and JEFFAMINE ED series compounds are polyether diamine based with a predominantly PEG (polyethylene glycol) backbone.

Other non-limiting examples of suitable alkoxylated polyamines in the diamine form include compounds corresponding to the following formula:

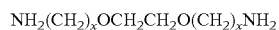

wherein x is 2 or 3.

Examples of alkoxylated polyamines are diamine compounds belonging to the JEFFAMINE series available from Huntsman Corporation, Salt Lake City, Utah, such as JEFFAMINE EDR148, and JEFFAMINE EDR176.

Additional non-limiting examples of alkoxylated polyamines in the triamine form include compounds corresponding to the following formula:

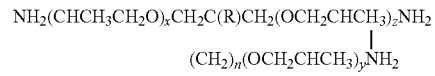

wherein R is hydrogen, —CH$_2$ or —C$_2$H$_5$, n=0 or 1, and x, y, and z independently of one another, represent numbers of from 0 to 100 and the sum of x+y+z is at least 1.

Examples of alkoxylated polyamines are triamine compounds belonging to the JEFFAMINE series such as the JEFFAMINE T series available from Huntsman Corporation, Salt Lake City, Utah. Examples of the JEFFAMINE T series compounds are JEFFAMINE T403, JEFFAMINE T3000, and JEFFAMINE T5000. JEFFAMINE T series compounds are triamines made by reacting PO with a triol initiator followed by aminating the terminal hydroxyl groups.

The total amount of the one or more amines may vary depending on the type of composition. In some cases, the total amount of the one or more amines is about 0.1 to about 35 wt. %, based on the total weight of the composition. In some cases, the total amount of the one or more amines is about 0.1 to about 30 wt. %, about 0.1 to about 25 wt. %, about 0.1 to about 20 wt. %, about 0.1 to about 15 wt. %, about 0.1 to about 10 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, or about 3 to about 8 wt. %.

Additional Components

Cationic Conditioning Compounds

The cationic conditioning agent employed in the compositions of the present invention can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic conditioning agents are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 in the CTFA Cosmetic Ingredient Dictionary, 3rd Ed., published in 1982 by the Cosmetic Toiletry and Fragrance Association, Inc. (hereafter CTFA Dictionary and CTFA name), is sold under the trademark MERQUAT-100, and is described as having a weight average molecular weight of approximately 100,000. A copolymer reaction product of dimethyldiallylammonium chloride with acrylamide monomers is named Polyquaternium-7 in the CTFA Dictionary, is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the CTFA name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the CTFA name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10 in the CTFA Dictionary. Also useful are quaternized copolymers of hydroxyethylcellulose and dimethyldimethylammonium chloride, having the CTFA name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconam idopropyldimethyl-2-hydroxyethyl-ammonium chloride and minkamidopropyldimethyl-2-hydroxyethylammonium chloride identified respectively by the CTFA names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the CTFA name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the CTFA name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

The total amount of the one or more conditioning agents, if present, may vary. In some cases, the total amount of the one or more conditioning agents is from about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Thickening Agents

The compositions may contain one or more thickeners or viscosity modifying agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

The total amount of the one or more thickening agents may vary, but in some cases is about 0.1 to about 15 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about wt. %, about 0.5 to about 5 wt. %, about 1 to about 10 wt. %, about 1 to about 8 wt. %, about 1 to about 6 wt. %, or about 1 to about 5 wt. %, based on the total weight of the composition.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair care formulations depending on the specific combination of other components, the form of the compositions, and/or the use of the formulation (e.g., hair spray, cream, conditioner, etc.).

Example Types of Active Compositions

Bleach Compositions

When hair lightening or color-altering uses separate bleach and developer compositions, the bleach composition may comprise at least one oxidizing agent chosen from persulfates, perborates, percarbonates, peracids, bromates, their salts, and mixtures thereof. In some instances, the at least one oxidizing agent is chosen from alkali metal salts of perborates, percarbonates, bromates, and persulfates, such as, for example, ammonium, sodium, and potassium salts. The bleach composition may also optionally comprise a cosmetically acceptable carrier.

The at least one oxidizing agent of the bleach compositions of the disclosure is utilized in an amount sufficient to lighten or "bleach" hair. By way of example only, the at least one oxidizing agent of the bleach composition may be present in an amount ranging from about 10% by weight to about 100% by weight, such as from about 20% to about 90% by weight, from about 30% to about 80% by weight, or from about 40% to about 75% by weight, based on the total weight of the bleach composition. In further embodiments, the at least one oxidizing agent of the bleach composition may be present in an amount ranging from about 5% to about 50%, such as about 10% to about 45%, or about 15% to about 40%. In some cases, the at least one oxidizing agent of the bleach composition may be present in an amount of at least 40% by weight, based on the total weight of the bleach composition.

The bleach composition may be in any form, such as, for example, in the form of a powder, gel, liquid, foam, lotion, cream, mousse, and emulsion.

In some cases, the bleach composition may be anhydrous. Optionally, water may be added as an activator, by mixing it with the bleach composition.

The bleach composition of the present disclosure may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The pH adjusters may, in various embodiments, be present in the bleach composition in an amount effective to provide the color-altering composition with a pH ranging from about 1 to about 7 when the bleach composition is combined with the developer composition. By way of example, the amount of pH adjuster may be present, in various embodiments, in an amount of at least about 0.01%, such as at least about 0.1%, at least about 0.2%, or at least about 0.5%.

In some cases, the bleach composition is acidic, with the pH ranging from about 1 to about 7; and in some cases, the bleach composition has a pH higher than about 7. When the bleach composition is in powder form, the pH may be measured in a 1% solution in water.

Colorants may also optionally be present in the bleach compositions. The colorants useful according to various embodiments of the disclosure are those colorants that are stable in the bleach composition, and can impart additional toning and coloring to hair. Exemplary hair colorants include, but are not limited to, pigments, liposoluble dyes, direct dyes, nacreous pigments, pearling agents, leuco dyes, optical lightening colorants, natural colorants and optically-variable pigments.

Developer Compositions

Developer compositions often include peroxide, such as hydrogen peroxide. The developer composition may also optionally comprise a cosmetically acceptable carrier. The hydrogen peroxide may be present in an amount of at least about 1% by weight, based on the total weight of the developer composition. In some cases, hydrogen peroxide is present in an amount ranging from about 0.1% to about 80% by weight, such as from about 1.0% to about 75% by weight, or from about 2% to about 10% by weight, based on the total weight of the developer composition. Furthermore, the hydrogen peroxide may be present in the developer composition in an amount ranging from about 2% to about 25%, such as about 4% to about 20%, about 6% to about 15%, or about 7% to about 10%.

The cosmetically acceptable carrier of the developer composition may, for example, be present in an amount ranging from about 0.5% to about 99% by weight, such as from about 5% to about 95% by weight, relative to the total weight of the developer composition.

The pH of the developer composition can range from about 1 to about 5, such as from about 2 to about 4, and it may be adjusted to the desired value using pH adjusters that are well known in the art in the cosmetic treatment of keratin fibers, including, for example, those described herein.

The developer composition may be in the form of a powder, gel, liquid, foam, lotion, cream, mousse, and emulsion.

Optionally, water may be added as an activator, by mixing it with the developer composition.

The developer composition may, in various cases, comprise additional components such as, for example, at least one auxiliary ingredient chosen from rheology-modifying agents, chelants, fatty substances, ceramides, alkoxyaminosilicones, and silanes, and any other component known in the art to be useful in a developer composition.

In some instances, the bleach composition and developer composition may be combined to form the lightening composition or color-altering composition in a ratio of bleach composition to developer composition ranging from about 1:1 to about 1:5, such as from about 1:1 to about 1:2, or about 1:2 to about 1:4.

Shape-Altering Compositions

Compositions for altering the shape of the hair comprise hair shaping agents for example, agents for straightening, relaxing, and/or shaping the hair. By way of example, hair shaping agents may optionally be chosen from inorganic hydroxides or organic hydroxides, for example sodium hydroxide, potassium hydroxide, lithium hydroxide, calcium hydroxide, or guanidine hydroxide, or may be chosen from organic amines and other non-hydroxide compounds. In some cases, the hair relaxing agents may be chosen from thiol compounds such as cysteine, cysteamine, N-substituted cysteamines, alkyl substituted mercaptoacetamides, dimercaptoadipic acid, thioglycerol, thiolactic acid, thioglycolic acid or its salts, (e.g., a thioglycolate), monothioglycolic acid esters such as diol esters of thioglycolic acid, glyceryl monothioglycolate, thiocholine or its salts, amino thiols, and thiols attached to low molecular weight polymers, sulfites such as sodium hyposulfite, and bisulfites such as ammonium or sodium bisulfite.

The hair shaping composition may also comprise a cosmetically acceptable carrier. The cosmetically acceptable carrier may, for example, be present in the shape-altering composition in an amount ranging from about 1% to about 40% by weight, such as from about 5% to about 35% by weight, or about 10% to about 30% by weight of the shape-altering composition.

In some cases, the hair shaping composition comprises or is used in conjunction with at least one neutralizer (for example, in a neutralizing composition), for example an oxidizing agent. Exemplary useful oxidizing agents include peroxides, bromates, and perborates, e.g., hydrogen peroxide, potassium bromate, sodium bromate and sodium perborate.

The shape-altering composition may be left on the hair for a period of time sufficient to achieve the desired alteration in hair shape. For example, the shape-altering composition may be left on the hair for up to one hour, such as from about 3 minutes to about 45 minutes, from about 5 minutes to about 30 minutes, or from about 10 minutes to about 20 minutes. In further embodiments, the shape-altering composition may be left on the hair for a period up to about 30 minutes, such as, for example, from about 1 to about 30 minutes, about 1 to about 10 minutes, or about 1 to about 5 minutes. One skilled in the art will, by considering various factors such as starting hair shape and desired hair shape, be able to determine an appropriate amount of time to leave the shape-altering composition on the hair in order to achieve the desired alternation in hair shape.

If desired, the shape-altering composition may, optionally, be shampooed and/or rinsed off the hair.

Forms

The compositions described herein may be in any suitable physical form. Suitable forms include, but are not limited to low to moderate viscosity liquids, lotions, milks, mousses, sprays, gels, creams, conditioners, and the like.

i. Spray

The compositions described herein for treating hair may be in the form of a spray. The spray typically includes a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant.

The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

ii. Conditioners

The compositions disclosed herein may be in the form of a conditioner. The conditioner may include one or more conditioning agents, such as cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

iii. Creams

The compositions disclosed herein for may be in the form of a cream.

Implementation of the present disclosure is provided by way of the following examples. The examples serve to illustrate the technology without being limiting in nature.

Example 1

| (Formulations) | | | | |
|---|---|---|---|---|
| Ingredients | 1 | 2 | 3 | 4 |
| Maleic Acid | 10.8 | 10.8 | — | — |
| Monoethanoloamine | 5.4 | 5.4 | 5.4 | — |
| PVM/MA Copolymer[1] | | 1.5 | 1.5 | 1.5 |
| Water | QS 100 | QS 100 | QS 100 | QS 100 |

[1]Present in the raw material known by the tradename STYLEZE XT3 and commercially available from Ashland. INCI Name: Aqua (and) Polyimide-1 (and) PVM/MA Copolymer (and) Caprylyl Glycol.

Example 2

Hair Lightening 15 grams of a bleach composition was mixed with 15 grams of a developer composition, and 4 grams of Formulation 1, 2, 3, or 4 of Example 1. Each of the four mixtures was separately applied to regular bleach hair swatches for 35 minutes. After 35 minutes, the swatches were rinsed with water, shampooed once, and blown dry. The components of the bleach composition and the developer composition are provided below.

| Bleach Composition | |
|---|---|
| Ingredient | wt. % |
| Magnesium Carbonate Hydroxide | 9 |
| Sodium Silicate | 17 |
| Disodium EDTA | 1 |
| Sodium Metasilicate | 3 |
| Surfactants | 11 |
| Potassium Persulfate | 50 |
| Ammonium Persulfate | 5 |
| Additives and Optional Ingredients | 4 |

| Developer Compositions | | |
|---|---|---|
| Ingredient | wt. % | wt. % |
| Sodium Stannate | 0.04 | 0.04 |
| Surfactants | 3.7 | 3.7 |
| Pentasodium Pentetate | 0.06 | 0.06 |
| Glycerin | 0.5 | 0.5 |
| Hydrogen Peroxide | 9 | 12 |
| Tetrasodium Pyrophosphate | 0.02 | 0.02 |
| Water | QS 100 | QS 100 |

The hair swatches were then evaluated by three independent experts for sensorial characteristics (combability, smoothness, and discipline). Each individual expert ranked the hair swatches according to a four point scale, where "1" represents the best result and "4" represents the worst result. All three experts arrived at the same conclusions, which are shown below.

| | Combability | Smoothness | Discipline |
|---|---|---|---|
| Control[1] | 4 | 4 | 4 |
| Formula 1 | 3 | 3 | 3 |
| Formula 2 | 2 | 2 | 2 |
| Formula 3 | 1 | 1 | 1 |
| Formula 4 | 1 | 1 | 1 |

[1]Hair bleached using only the combination of bleach powder and bleach developer (1:1 ratio) (no maleic acid, no monoethanolamine, no maleic acid polymer).

Hair bleached with no additive (Control) provided the worst cosmetic properties as it was most difficult to comb, roughest, and had the least amount of discipline. The addition of maleic acid and monoethanol amine, as with Formula 1, provided minor improvements to cosmetic properties. However, the addition of a polymeric acid compounds and/or polymeric acid anhydride compound (PVM/MA copolymer), as with Formula 2, provided significant improvement. Removal of maleic acid, as with Formula 3, and monoethanol amine, as with Formula 4 demonstrated the highest level of cosmeticity. This indicates that chemical treatments containing a polymeric acid compounds and/or polymeric acid anhydride compound (PVM/MA copolymer), either in its natural state (Formula 4) or neutralized with amine (Formula 3), provides surprisingly good cosmetic properties.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat" (and its grammatical variations) as used herein also refers to contacting keratinous substrates such as hair with the compositions of the present disclosure.

A "rinse-off" product refers to a composition such as a hair care composition that is rinsed and/or washed with water either after or during the application of the composition onto the keratinous substrate, and before drying and/or styling said keratinous substrate. At least a portion of the composition is removed from the keratinous substrate during the rinsing and/or washing.

The term "stable" as used herein means that the composition does not exhibit phase separation and/or crystallization.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair-lightening composition comprising:
    (a) polyvinyl methyl ether/maleic acid copolymer;
    (b) hydrogen peroxide; and
    (c) one or more persulfates.

2. The hair-lightening composition of claim 1, wherein the (a) polyvinyl methyl ether/maleic acid copolymer is present in an amount ranging from about 0.01 to about 25 wt. %, based on the total weight of the hair-lightening composition.

3. The hair-lightening composition of claim 1, wherein the (a) polyvinyl methyl ether/maleic acid copolymer is present in an amount ranging from about 0.1 to about 10 wt. %, based on the total weight of the hair-lightening composition.

4. The hair-lightening composition of claim 1, wherein the composition is essentially free of VP/DMAPA acrylates copolymer.

5. A method for lightening hair comprising:
    i. applying to the hair a hair-lightening composition of claim 1; and
    ii. allowing the hair-lightening composition of claim 1 to remain on the hair for about 1 to about 45 minutes.

6. The method of claim 5 carried out at a temperature ranging from 10° C. to 50° C.

7. The method of claim 5, further comprising:
    iii) rinsing the hair with water, and optionally shampooing the hair.

8. The method of claim 5 carried out at a temperature ranging from 20° C. to 30° C.

9. The method of claim 5, wherein the hair-lightening composition is allowed to remain on the hair for about 1 minute to about 30 minutes.

10. The method of claim 5, wherein the method is carried out without applying heat during treatment.

11. The method of claim 5, wherein the method is carried out without applying heat after treatment.

12. The method of claim 5, wherein the (a) polyvinyl methyl ether/maleic acid copolymer is present in an amount ranging from about 0.01 to about 25 wt. %, based on the total weight of the hair-lightening composition.

13. The method of claim 5, wherein the (a) polyvinyl methyl ether/maleic acid copolymer is present in an amount ranging from about 0.1 to about 10 wt. %, based on the total weight of the hair-lightening composition.

14. The method of claim 5, wherein the hair-lightening composition is essentially free of VP/DMAPA acrylates copolymer.

* * * * *